(12) United States Patent
Andries et al.

(10) Patent No.: US 8,691,800 B2
(45) Date of Patent: *Apr. 8, 2014

(54) QUINOLINE DERIVATIVES AS ANTIBACTERIAL AGENTS

(75) Inventors: Koenraad Jozef Lodewijk Marcel Andries, Beerse (BE); Anil Koul, Berchem (BE); Jérôme Emile Georges Guillemont, Ande (FR); Elisabeth Thérèse Jeanne Pasquier, Le Neubourg (FR)

(73) Assignee: Janssen Pharmaceutica N.V., Beerse (BE)

( * ) Notice: Subject to any disclaimer, the term of this patent is extended or adjusted under 35 U.S.C. 154(b) by 606 days.

This patent is subject to a terminal disclaimer.

(21) Appl. No.: 11/997,015

(22) PCT Filed: Jul. 31, 2006

(86) PCT No.: PCT/EP2006/064847
§ 371 (c)(1),
(2), (4) Date: Jan. 28, 2008

(87) PCT Pub. No.: WO2007/014934
PCT Pub. Date: Feb. 8, 2007

(65) Prior Publication Data
US 2008/0227775 A1     Sep. 18, 2008

(30) Foreign Application Priority Data

Aug. 3, 2005   (EP) ................................ 05107155

(51) Int. Cl.
*A61K 31/33* (2006.01)
(52) U.S. Cl.
USPC ........................................................ 514/183
(58) Field of Classification Search
USPC ........................................................ 514/183
See application file for complete search history.

(56) References Cited

U.S. PATENT DOCUMENTS 5,965,572 A * 10/1999 Ellis et al. .................... 514/311

FOREIGN PATENT DOCUMENTS

WO   WO 00/34265    *  6/2000 ........... C07D 401/00
WO   WO 02/056882 A1 *  7/2002 ............. A61K 31/33
(Continued)

OTHER PUBLICATIONS

Andries, K. et al., "A Diarylquinoline Drug Active on the ATP Synthase of *Mycobacterium tuberculosis*", Science, American Association for the Advancement of Science, US., vol. 307, Jan. 14, 2005, pp. 223-227, XP002358962, ISSN: 0036-8075 cited in the application, p. 224, left-hand column.

(Continued)

*Primary Examiner* — Brandon Fetterolf
*Assistant Examiner* — Christopher R Stone
(74) *Attorney, Agent, or Firm* — Thomas J. Dodd

(57) ABSTRACT

Use of a compound for the manufacture of a medicament for the treatment of a bacterial infection provided that the bacterial infection is other than a Mycobacterial infection, said compound being a compound of Formula (Ia) or (Ib)

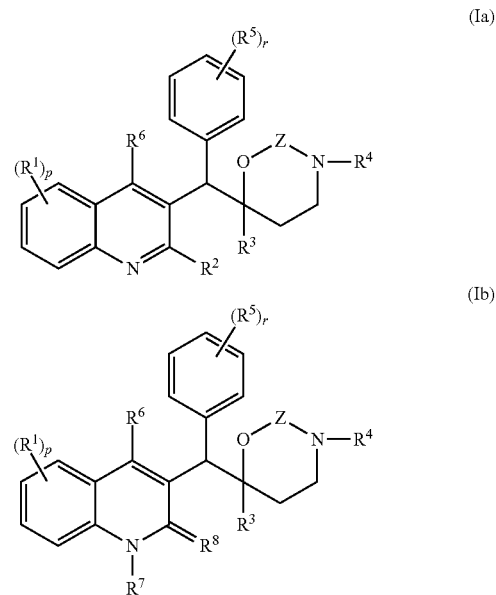

a pharmaceutically acceptable acid or base addition salt thereof, a quaternary amine thereof, a stereochemically isomeric form thereof, a tautomeric form thereof or a N-oxide form thereof, wherein $R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl; p is 1, 2, 3 or 4; $R^2$ is hydrogen, hydroxy, thio, alkyloxy, alkyloxyalkyloxy, alkylthio, mono or di(alkyl)amino or a radical of formula

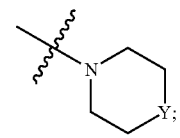

$R^3$ is alkyl, Ar, Ar-alkyl, Het or Het-alkyl; $R^4$ is hydrogen, alkyl or benzyl; $R^5$ is hydrogen, halo, haloalkyl, hydroxy, Ar, alkyl, alkyloxy, alkylthio, alkyloxyalkyl, alkylthioalkyl, Ar-alkyl or di(Ar)alkyl; or two vicinal $R^5$ radicals may be taken together to form together with the phenyl ring to which they are attached a naphthyl; r is 1, 2, 3, 4 or 5; $R^6$ is hydrogen, alkyl, Ar or Het; $R^7$ is hydrogen or alkyl; $R^5$ is oxo; or $R^7$ and $R^5$ together form the radical —CH=CH—N=; Z is $CH_2$ or C(=O).

19 Claims, No Drawings

(56) References Cited

FOREIGN PATENT DOCUMENTS

| WO | WO 2004/002490 A2 * | 1/2004 | ........... A61K 31/535 |
| WO | WO 2004/011436 A | 2/2004 | |
| WO | WO 2005/070924 A | 8/2005 | |
| WO | WO 2007/014934 A2 | 2/2007 | |

OTHER PUBLICATIONS

International Search Report dated Mar. 17, 2006 for related International Application No. PCT/EP2006/064847.

* cited by examiner

QUINOLINE DERIVATIVES AS ANTIBACTERIAL AGENTS

CROSS REFERENCE TO RELATED APPLICATIONS

This application is a national stage application of Patent Application No. PCT/EP2006/064847, filed Jul. 31, 2006, which in turn claims the benefit of EPO Patent Application No. 05107155.3, filed Aug. 3, 2005. The complete disclosures of the aforementioned related patent applications are hereby incorporated herein by reference for all purposes.

The present invention relates to the use of quinoline derivatives for the manufacture of a medicament for the treatment of a bacterial infection.

Resistance to first-line antibiotic agents is an emerging problem. Some important examples include penicillin-resistant *Streptococcus pneumoniae*, vancomycin-resistant enterococci, methicillin-resistant *Staphylococcus aureus*, multi-resistant salmonellae.

The consequences of resistance to antibiotic agents are severe. Infections caused by resistant microbes fail to respond to treatment, resulting in prolonged illness and greater risk of death. Treatment failures also lead to longer periods of infectivity, which increase the numbers of infected people moving in the community and thus exposing the general population to the risk of contracting a resistant strain infection. Hospitals are a critical component of the antimicrobial resistance problem worldwide. The combination of highly susceptible patients, intensive and prolonged antimicrobial use, and cross-infection has resulted in infections with highly resistant bacterial pathogens.

Self-medication with antimicrobials is another major factor contributing to resistance. Self-medicated antimicrobials may be unnecessary, are often inadequately dosed, or may not contain adequate amounts of active drug.

Patient compliance with recommended treatment is another major problem. Patients forget to take medication, interrupt their treatment when they begin to feel better, or may be unable to afford a full course, thereby creating an ideal environment for microbes to adapt rather than be killed.

Because of the emerging resistance to multiple antibiotics, physicians are confronted with infections for which there is no effective therapy. The morbidity, mortality, and financial costs of such infections impose an increasing burden for health care systems worldwide.

Therefore, there is a high need for new compounds to treat bacterial infections, especially for the treatment of infections caused by resistant strains.

Substituted quinolines were already disclosed in U.S. Pat. No. 5,965,572 (The United States of America) for treating antibiotic resistant infections and in WO 00/34265 to inhibit the growth of bacterial microorganisms.

WO 2004/011436, WO2005/070924, WO2005/070430 and WO2005/075428 disclose substituted quinoline derivatives having activity against *Mycobacteria*, in particular against *Mycobacterium tuberculosis*. One particular compound of these substituted quinoline derivatives is described in Science (2005), 307, 223-227. None of these publications disclose the use of the present substituted quinoline derivatives according to this invention.

SUMMARY OF THE INVENTION

The present invention relates to the use of a compound for the manufacture of a medicament for the treatment of a bacterial infection, said compound being a compound of Formula (Ia) and (Ib)

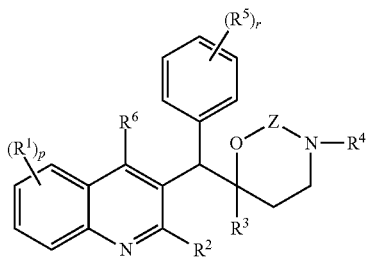

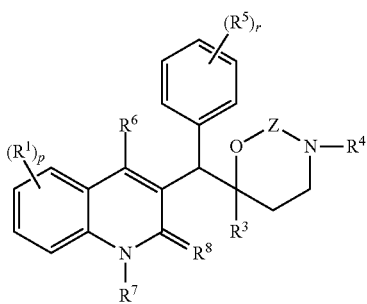

a pharmaceutically acceptable acid or base addition salt thereof, a quaternary amine thereof, a stereochemically isomeric form thereof, a tautomeric form thereof or a N-oxide form thereof, wherein $R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl;

p is an integer equal to 1, 2, 3 or 4

$R^2$ is hydrogen, hydroxy, mercapto, alkyloxy, alkyloxyalkyloxy, alkylthio, mono or di(alkyl)amino or a radical of formula

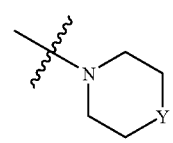

wherein Y is $CH_2$, O, S, NH or N-alkyl;

$R^3$ is alkyl, Ar, Ar-alkyl, Het or Het-alkyl;

$R^4$ is hydrogen, alkyl or benzyl;

$R^5$ is hydrogen, halo, haloalkyl, hydroxy, Ar, alkyl, alkyloxy, alkylthio, alkyloxyalkyl, alkylthioalkyl, Ar-alkyl or di(Ar)alkyl; or two vicinal $R^5$ radicals may be taken together to form together with the phenyl ring to which they are attached a naphthyl;

r is an integer equal to 1, 2, 3, 4 or 5; and $R^6$ is hydrogen, alkyl, Ar or Het;

$R^7$ is hydrogen or alkyl;

$R^5$ is oxo; or $R^7$ and $R^8$ together form the radical $CH=CH-N=$;

Z is $CH_2$ or $C(=O)$;

alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with hydroxy, alkyloxy or oxo;

Ar is a homocycle selected from the group of phenyl, naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, aminocarbonyl, morpholinyl and mono- or dialkylaminocarbonyl;

Het is a monocyclic heterocycle selected from the group of N-phenoxypiperidinyl, piperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from the group of quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents, each substituent independently selected from the group of halo, hydroxy, alkyl or alkyloxy;

halo is a substituent selected from the group of fluoro, chloro, bromo and iodo and haloalkyl is a straight or branched saturated hydrocarbon radical having from 1 to 6 carbon atoms or a cyclic saturated hydrocarbon radical having from 3 to 6 carbon atoms or a cyclic saturated hydrocarbon radical having from 3 to 6 carbon atoms attached to a straight or branched saturated hydrocarbon radical having from 1 to 6 carbon atoms; wherein one or more carbon atoms are substituted with one or more halo atoms;

provided that the bacterial infection is other than a Mycobacterial infection.

The present invention also relates to a method of treating a bacterial infection provided that the bacterial infection is other than a Mycobacterial infection, in a mammal, in particular a warm-blooded mammal, more in particular a human, comprising administering an effective amount of a compound of the invention to the mammal.

The compounds according to Formula (Ia) and (Ib) are interrelated in that e.g. a compound according to Formula (Ib), with $R^8$ equal to oxo is the tautomeric equivalent of a compound according to Formula (Ia) with $R^2$ equal to hydroxy (keto-enol tautomerism).

DETAILED DESCRIPTION

In the framework of this application, alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with hydroxy, alkyloxy or oxo.

Preferably, alkyl is methyl, ethyl or cyclohexylmethyl.

An interesting embodiment of alkyl in all definitions used hereinbefore or hereinafter including haloalkyl, is $C_{1-6}$alkyl which represents a straight or branched saturated hydrocarbon radical having from 1 to 6 carbon atoms such as for example methyl, ethyl, propyl, 2-methyl-ethyl, pentyl, hexyl and the like. A preferred subgroup of $C_{1-6}$alkyl is $C_{1-4}$alkyl which represents a straight or branched saturated hydrocarbon radical having from 1 to 4 carbon atoms such as for example methyl, ethyl, propyl, 2-methylethyl and the like.

In the framework of this application, Ar is a homocycle selected from the group of phenyl, naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, aminocarbonyl, morpholinyl and mono- or dialkylaminocarbonyl. Preferably, Ar is naphthyl or phenyl, each optionally substituted with 1 or 2 halo substituents.

In the framework of this application, Het is a monocyclic heterocycle selected from the group of N-phenoxypiperidinyl, piperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from the group of quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents, each substituent independently selected from the group of halo, hydroxy, alkyl or alkyloxy. Preferably, Het is thienyl or furanyl or pyridyl, most preferably Het is furanyl.

In the framework of this application, halo is a substituent selected from the group of fluoro, chloro, bromo and iodo and haloalkyl is a straight or branched saturated hydrocarbon radical having from 1 to 6 carbon atoms or a cyclic saturated hydrocarbon radical having from 3 to 6 carbon atoms or a cyclic saturated hydrocarbon radical having from 3 to 6 carbon atoms attached to a straight or branched saturated hydrocarbon radical having from 1 to 6 carbon atoms; wherein one or more carbon atoms are substituted with one or more halo atoms. Preferably, halo is bromo, fluoro or chloro and preferably, haloalkyl is polyhalo$C_{1-6}$alkyl which is defined as mono- or polyhalosubstituted $C_{1-6}$alkyl, for example, methyl with one or more fluoro atoms, for example, difluoromethyl or trifluoromethyl, 1,1-difluoro-ethyl and the like. In case more than one halo atom is attached to an alkyl group within the definition of haloalkyl or polyhalo$C_{1-6}$alkyl, they may be the same or different.

In the definition of Het, it is meant to include all the possible isomeric forms of the heterocycles, for instance, pyrrolyl comprises 1H-pyrrolyl and 2H-pyrrolyl.

The Ar or Het listed in the definitions of the substituents of the compounds of Formula (Ia) or (Ib) (see for instance $R^3$) as mentioned hereinbefore or hereinafter may be attached to the remainder of the molecule of Formula (Ia) or (Ib) through any ring carbon or heteroatom as appropriate, if not otherwise specified. Thus, for example, when Het is imidazolyl, it may be 1-imidazolyl, 2-imidazolyl, 4-imidazolyl and the like.

Lines drawn from substituents into ring systems indicate that the bond may be attached to any of the suitable ring atoms.

The pharmaceutically acceptable acid addition salts are defined to comprise the therapeutically active non-toxic acid addition salt forms which the compounds according to either Formula (Ia) or (Ib) are able to form. Said acid addition salts can be obtained by treating the base form of the compounds according to either Formula (Ia) or (Ib) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicyclic acid, p-aminosalicylic acid and pamoic acid.

The compounds according to either Formula (Ia) or (Ib) containing acidic protons may also be converted into their therapeutically active non-toxic base addition salt forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said acid or base addition salt forms can be converted into the free forms by treatment with an appropriate base or acid.

The term addition salt as used in the framework of this application also comprises the solvates which the compounds according to either Formula (Ia) or (Ib) as well as the salts thereof, are able to form. Such solvates are, for example, hydrates and alcoholates.

The term "quaternary amine" as used hereinbefore defines the quaternary ammonium salts which the compounds of formula (Ia) or (Ib) are able to form by reaction between a basic nitrogen of a compound of formula (Ia) or (Ib) and an appropriate quaternizing agent, such as, for example, an optionally substituted alkylhalide, arylalkylhalide, alkylcarbonylhalide, Arcarbonylhalide, Hetalkylhalide or Hetcarbonylhalide, e.g. methyliodide or benzyliodide. Preferably, Het represents a monocyclic heterocycle selected from furanyl or thienyl; or a bicyclic heterocycle selected from benzofuranyl or benzothienyl; each monocyclic and bicyclic heterocycle may optionally be substituted with 1, 2 or 3 substituents, each substituent independently selected from the group of halo, alkyl and Ar. Preferably, the quaternizing agent is alkylhalide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate, acetate, triflate, sulfate, sulfonate. Preferably, the counterion is iodo. The counterion of choice can be introduced using ion exchange resins.

Compounds of either Formula (Ia) or (Ib) and some of the intermediate compounds invariably have at least two stereogenic centers in their structure which may lead to at least 4 stereochemically different structures.

The term "stereochemically isomeric forms" as used herein defines all possible isomeric forms which the compounds of either Formula (Ia) or (Ib) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Stereochemically isomeric forms of the compounds of either Formula (Ia) or (Ib) are obviously intended to be embraced within the scope of this invention. Following CAS-nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

When a specific stereoisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s). Thus, when a compound of Formula (Ia) or (Ib) is for instance specified as (αS, βR), this means that the compound is substantially free of the (αR, βS) isomer.

The compounds of either Formula (Ia) and (Ib) may be synthesized in the form of racemic mixtures of enantiomers which can be separated from one another following art-known resolution procedures. The racemic compounds of either Formula (Ia) and (Ib) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of either Formula (Ia) and (Ib) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The tautomeric forms of the compounds of either Formula (Ia) or (Ib) are meant to comprise those compounds of either Formula (Ia) or (Ib) wherein e.g. an enol group is converted into a keto group (keto-enol tautomerism).

The N-oxide forms of the compounds according to either Formula (Ia) or (Ib) are meant to comprise those compounds of either Formula (Ia) or (Ib) wherein one or several nitrogen atoms are oxidized to the so-called N-oxide, particularly those N-oxides wherein the nitrogen of the amine radical is oxidized.

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems*, 1985, pp. 112-176, and *Drugs*, 1985, 29, pp. 455-473.

Pro-drugs forms of the pharmacologically-active compounds according to the invention will generally be compounds according to either Formula (Ia) or (Ib), the pharmaceutically acceptable acid or base addition salts thereof, the stereochemically isomeric forms thereof, the tautomeric forms thereof and the N-oxide forms thereof, having an acid group which is esterified or amidated. Included in such esterified acid groups are groups of the formula —COOR$^x$, where R$^x$ is a C$_{1-6}$alkyl, phenyl, benzyl or one of the following groups:

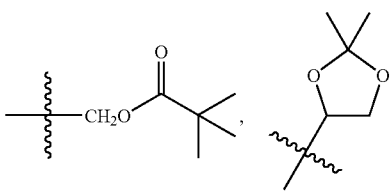

Amidated groups include groups of the formula —CONR$^y$R$^z$, wherein R$^y$ is H, C$_{1-6}$alkyl, phenyl or benzyl and R$^z$ is OH, H, C$_{1-6}$alkyl, phenyl or benzyl.

Compounds according to the invention having an amino group may be derivatised with a ketone or an aldehyde such as formaldehyde to form a Mannich base. This base will hydrolyze with first order kinetics in aqueous solution.

Whenever used hereinafter, the term "compounds of Formula (Ia) or (Ib)" is meant to also include their N-oxide forms, their salts, their quaternary amines, their tautomeric forms or their stereochemically isomeric forms. Of special interest are those compounds of Formula (Ia) or (Ib) which are stereochemically pure.

An interesting embodiment of the present invention relates to those compounds of Formula (Ia) or (Ib), the pharmaceutically acceptable acid or base addition salts thereof, the stereochemically isomeric forms thereof, the tautomeric forms thereof and the N-oxide forms thereof, wherein Z is CH$_2$;
R$^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl;
p is an integer equal to 1, 2, 3 or 4;
R$^2$ is hydrogen, hydroxy, mercapto, alkyloxy, alkyloxyalkyloxy, alkylthio, mono or di(alkyl)amino or a radical of formula

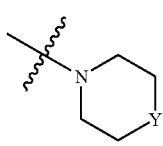

wherein Y is CH$_2$, O, S, NH or N-alkyl;
R$^3$ is alkyl, Ar, Ar-alkyl, Het or Het-alkyl;
R$^4$ is hydrogen, alkyl or benzyl;
R$^5$ is hydrogen, halo, haloalkyl, hydroxy, Ar, alkyl, alkyloxy, alkylthio, alkyloxyalkyl, alkylthioalkyl, Ar-alkyl or di(Ar)alkyl; or
two vicinal R$^5$ radicals may be taken together to form together with the phenyl ring to which they are attached a naphthyl;
r is an integer equal to 1, 2, 3, 4 or 5; and
R$^6$ is hydrogen, alkyl, Ar or Het;
R$^7$ is hydrogen or alkyl
R$^8$ is oxo; or
R$^7$ and R$^8$ together form the radical CH=CH—N=;

alkyl is a straight or branched saturated hydrocarbon radical having from 1 to 6 carbon atoms; or is a cyclic saturated hydrocarbon radical having from 3 to 6 carbon atoms; or is a a cyclic saturated hydrocarbon radical having from 3 to 6 carbon atoms attached to a straight or branched saturated hydrocarbon radical having from 1 to 6 carbon atoms; wherein each carbon atom can be optionally substituted with halo, hydroxy, alkyloxy or oxo;

Ar is a homocycle selected from the group of phenyl, naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, aminocarbonyl, morpholinyl and mono- or dialkylaminocarbonyl;

Het is a monocyclic heterocycle selected from the group of N-phenoxypiperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from the group of quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents selected from the group of halo, hydroxy, alkyl or alkyloxy;

halo is a substituent selected from the group of fluoro, chloro, bromo and iodo and haloalkyl is a straight or branched saturated hydrocarbon radical having from 1 to 6 carbon atoms or a cyclic saturated hydrocarbon radical having from 3 to 6 carbon atoms, wherein one or more carbonatoms are substituted with one or more halo-atoms.

Preferably, the invention relates to a compound of Formula (Ia) or (Ib) or any subgroup thereof as mentioned hereinbefore as interesting embodiment wherein R$^5$ is hydrogen, halo, haloalkyl, hydroxy, Ar, alkyl, alkyloxy, alkylthio, alkyloxyalkyl, alkylthioalkyl, Ar-alkyl or di(Ar)alkyl.

Preferably, the invention relates to compounds of Formula (Ia) or (Ib) wherein:
R$^1$ is hydrogen, halo, cyano, Ar, Het, alkyl, and alkyloxy;
p is an integer equal to 1, 2, 3 or 4;
R$^2$ is hydrogen, hydroxy, alkyloxy, alkyloxyalkyloxy, alkylthio or a radical of formula

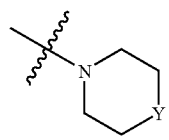

wherein Y is O;
R$^3$ is alkyl, Ar, Ar-alkyl or Het;
R$^4$ is hydrogen, alkyl or benzyl;
R$^5$ is hydrogen, halo or alkyl; or
two vicinal R$^5$ radicals may be taken together to form together with the phenyl ring to which they are attached a naphthyl;
r is an integer equal to 1; and
R$^6$ is hydrogen;
R$^7$ is hydrogen or alkyl;
R$^8$ is oxo; or
R$^7$ and R$^8$ together form the radical CH=CH—N=;

alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with halo or hydroxy;

Ar is a homocycle selected from the group of phenyl, naphthyl, acenaphthyl, tetrahydronaphthyl, each optionally substituted with 1, 2 or 3 substituents, each substituent independently selected from the group of halo, haloalkyl, cyano, alkyloxy and morpholinyl;

Het is a monocyclic heterocycle selected from the group of N-phenoxypiperidinyl, furanyl, thienyl, pyridinyl, pyrimidinyl; or a bicyclic heterocycle selected from the group of benzothienyl, 2,3-dihydrobenzo[1,4]dioxinyl or benzo[1,3]-dioxolyl; each monocyclic and bicyclic heterocycle may optionally be substituted on a carbon atom with 1, 2 or 3 alkyl substituents; and halo is a substituent selected from the group of fluoro, chloro and bromo.

For compounds according to either Formula (Ia) or (Ib), preferably the invention relates to a compound of Formula (Ia) or (Ib) or any subgroup thereof as mentioned hereinbefore as interesting embodiment wherein $R^1$ is hydrogen, halo, Ar, Het, alkyl or alkyloxy. More preferably, $R^1$ is halo. Most preferably, $R^1$ is bromo.

Preferably, the invention relates to a compound of Formula (Ia) or (Ib) or any subgroup thereof as mentioned hereinbefore as interesting embodiment wherein p is equal to 1.

Preferably, the invention relates to a compound of Formula (Ia) or (Ib) or any subgroup thereof as mentioned hereinbefore as interesting embodiment wherein $R^2$ is hydrogen, alkyloxy or alkylthio. More preferably, $R^2$ is alkyloxy. Most preferably, $R^2$ is methyloxy.

Preferably, the invention relates to a compound of Formula (Ia) or (Ib) or any subgroup thereof as mentioned hereinbefore as interesting embodiment wherein $R^3$ is naphthyl, phenyl or Het, in particular naphthyl or phenyl, each optionally substituted with 1 or 2 substituents, that substituent preferably being a halo or haloalkyl, most preferably being a halo. More preferably, $R^3$ is naphthyl or phenyl. Most preferably, $R^3$ is naphthyl. Or preferably, the invention relates to a compound of Formula (Ia) or (Ib) or any subgroup thereof as mentioned hereinbefore as interesting embodiment wherein $R^3$ is alkyl, Ar or Ar-alkyl.

Preferably, the invention relates to a compound of Formula (Ia) or (Ib) or any subgroup thereof as mentioned hereinbefore as interesting embodiment wherein $R^4$ is hydrogen or alkyl, more preferably alkyl, such as methyl or ethyl. Most preferably $R^4$ is methyl.

Preferably, the invention relates to a compound of Formula (Ia) or (Ib) or any subgroup thereof as mentioned hereinbefore as interesting embodiment wherein $R^5$ is hydrogen, alkyl or halo. More preferably, $R^5$ is hydrogen or halo, most preferably $R^5$ is hydrogen.

Preferably, the invention relates to a compound of Formula (Ia) or (Ib) or any subgroup thereof as mentioned hereinbefore as interesting embodiment wherein r is 1 or 2, more preferably 1.

Preferably, the invention relates to a compound of Formula (Ia) or (Ib) or any subgroup thereof as mentioned hereinbefore as interesting embodiment wherein $R^6$ is hydrogen or methyl. Most preferably, $R^6$ is hydrogen.

Preferably, the invention relates to a compound of Formula (Ia) or (Ib) or any subgroup thereof as mentioned hereinbefore as interesting embodiment wherein Z is $CH_2$.

Preferably, the invention relates to a compound of Formula (Ia) or (Ib) or any subgroup thereof as mentioned hereinbefore as interesting embodiment wherein the compound of formula (Ia) or (Ib) is a compound of the following formula

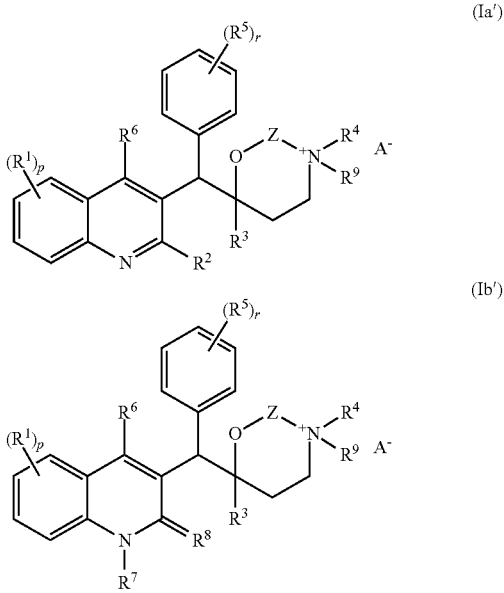

wherein $R^9$ represents alkyl, alkylcarbonyl, Ar, Ar-alkyl, Ar-carbonyl, $Het^1$-alkyl or $Het^1$-carbonyl; wherein $Het^1$ is a monocyclic heterocylce selected from furanyl or thienyl; or a bicyclic heterocycle selected from benzofuranyl or benzothienyl; each monocyclic and bicyclic heterocycle may optionally be substituted with 1, 2 or 3 substituents, each substituent independently selected from the group of halo, alkyl and Ar; and $A^-$ is a pharmaceutically acceptable counter ion, such as for example halo, e.g. chloro, bromo, iodo; trifluoroacetate; acetate; triflate; sulfate; sulfonate.

Preferably, in the compounds of Formula (Ia') or (Ib') $R^9$ is alkyl, in particular methyl or ethyl, more in particular methyl.

Preferably, in the compounds of Formula (Ia') or (Ib') $A^-$ is halo, in particular iodo.

For compounds according to Formula (Ib) only, preferably, the invention relates to a compound of Formula (Ia) or (Ib) or any subgroup thereof as mentioned hereinbefore as interesting embodiment wherein $R^7$ is alkyl, preferably methyl, and $R^8$ is oxygen.

An interesting group of compounds are the compounds of Formula (Ia), the pharmaceutically acceptable acid or base addition salts thereof, the quaternary amines thereof, the stereochemically isomeric forms thereof, the tautomeric forms thereof or the N-oxide forms thereof.

An interesting group of compounds are those compounds according to Formula (Ia), the pharmaceutically acceptable acid or base addition salts thereof, the quaternary amines thereof, the stereochemically isomeric forms thereof, the tautomeric forms thereof or the N-oxide forms thereof, in which $R^1$ is hydrogen, halo, Ar, Het, alkyl or alkyloxy; p=1; $R^2$ is hydrogen, alkyloxy or alkylthio, in particular alkyloxy; $R^3$ is naphthyl, phenyl or Het, each optionally substituted with 1 or 2 substituents selected from the group of halo and haloalkyl, in particular halo; $R^4$ is hydrogen or alkyl, in particular alkyl; $R^5$ is hydrogen, alkyl or halo, in particular hydrogen or halo; r is equal to 1 and $R^6$ is hydrogen.

An interesting group of compounds are those compounds according to Formula (Ia) wherein $R^1$ is hydrogen; halo, e.g. bromo; alkyl, e.g. methyl; Ar, e.g. phenyl, or Het, e.g. furanyl; $R^2$ is alkyloxy, e.g. methyloxy; $R^3$ is naphthyl, phenyl or Het, in particular naphthyl or phenyl, each optionally substituted with 1 or 2 halo, e.g. phenyl optionally substituted with 1 or 2 halo, or naphthyl; $R^4$ is alkyl, e.g. methyl or ethyl; $R^5$ is hydrogen or halo, e.g. chloro; $R^6$ is hydrogen; Z is $CH_2$ or $C(=O)$, in particular $CH_2$.

An interesting embodiment is the use of a compound of Formula (Ia) or (Ib) or any subgroup thereof as mentioned hereinbefore as interesting embodiment for the manufacture of a medicament for the treatment of an infection with a gram-positive and/or a gram-negative bacterium.

An interesting embodiment is the use of a compound of Formula (Ia) or (Ib) or any subgroup thereof as mentioned hereinbefore as interesting embodiment for the manufacture of a medicament for the treatment of an infection with a gram-positive bacterium.

An interesting embodiment is the use of the compounds of Formula (Ia) or (Ib) or any subgroup thereof as mentioned hereinbefore as interesting embodiment for the manufacture of a medicament for the treatment of an infection with a gram-negative bacterium.

An interesting embodiment is the use of a compound of Formula (Ia) or (Ib) or any subgroup thereof as mentioned hereinbefore as interesting embodiment for the manufacture of a medicament for the treatment of a bacterial infection wherein the compound of Formula (Ia) or (Ib) has a $IC_{90}<15$ µl/ml against at least one bacterium, in particular a gram-positive bacterium, preferably a $IC_{90}<10$ µl/ml, more preferably a $IC_{90}<5$ µl/ml; the $IC_{90}$ value being determined as described hereinafter.

Preferably, in the compounds of formula (Ia) and (Ib) or any subgroup thereof as mentioned hereinbefore as interesting embodiment, the term "alkyl" represents $C_{1-6}$alkyl, more preferably $C_{1-4}$alkyl.

Preferred compounds are compounds 1 to 21 as described hereinafter, a pharmaceutically acceptable acid or base addition salt thereof, a quaternary amine thereof, a stereochemically isomeric form thereof, a tautomeric form thereof or a N-oxide form thereof.

The present invention also relates to the following compounds

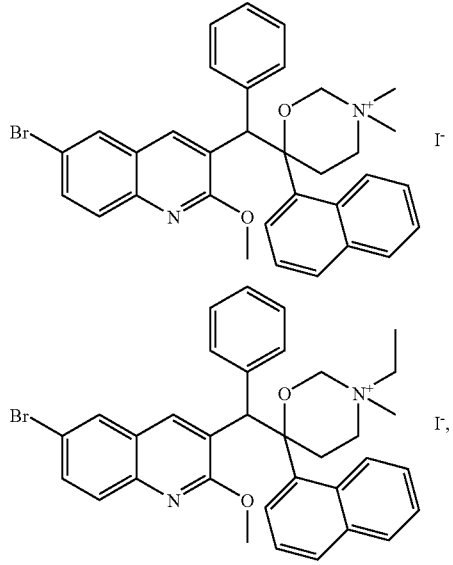

a stereochemically isomeric form thereof or a N-oxide form thereof.

Preferably, the compound of formula (Ia) or (Ib) is a particular diastereoisomer (substantially free of the other diastereoisomer(s)). In case the compound of formula (Ia) or (Ib) has two chiral centers this means that the compound is a racemic mixture of the (R,S) and (S,R) enantiomers or a racemic mixture of the (R,R) and (S,S) enantiomer. Hereinafter, the racemic mixtures of 2 enantiomers are indicated as diastereoisomer A or B. Whether the racemic mixture is indicated as A or B depends on whether it is first isolated in the synthesis protocol (i.e. A) or second (i.e. B). More preferably, the compound of formula (Ia) or (Ib) is a particular enantiomer (substantially free of the other enantiomers). In case the compound of formula (Ia) or (Ib) has two chiral centers this means that the compound is the (R,S), (S,R), (R,R) or (S,S) enantiomer. Hereinafter, said particular enantiomers are indicated as A1, A2, B1 or B2. Whether the enantiomer is indicated as A1, A2, B1 or B2 depends on whether it is isolated first or second in the synthesis protocol.

In general, bacterial pathogens may be classified as either gram-positive or gram-negative pathogens. Antibiotic compounds with activity against both gram-positive and gram-negative pathogens are generally regarded as having a broad spectrum of activity. The compounds of the present invention are regarded as active against gram-positive and/or gram-negative bacterial pathogens. In particular, the present compounds are active against at least one gram-positive bacterium, preferably against several gram-positive bacteria, more preferably against one or more gram-positive bacteria and/or one or more gram-negative bacteria.

The present compounds have bactericidal or bacteriostatic activity.

Examples of gram-positive and gram-negative aerobic and anaerobic bacteria, include Staphylococci, for example *S. aureus*; Enterococci, for example *E. faecalis*; Streptococci, for example *S. pneumoniae, S. mutans, S. pyogenes*; Bacilli, for example *Bacillus subtilis*; *Listeria*, for example *Listeria monocytogenes*; *Haemophilus*, for example *H. influenza*; *Moraxella*, for example *M. catarrhalis*; *Pseudomonas*, for example *Pseudomonas aeruginosa*; and *Escherichia*, for example *E. coli*. Gram-positive pathogens, for example Staphylococci, Enterococci and Streptococci are particularly important because of the development of resistant strains which are both difficult to treat and difficult to eradicate from for example a hospital environment once established. Examples of such strains are methicillin resistant *Staphylococcus aureus* (MRSA), methicillin resistant coagulase negative staphylococci (MRCNS), penicillin resistant *Streptococcus pneumoniae* and multiple resistant *Enterococcus faecium*.

The compounds of the present invention also show activity against resistant bacterial strains.

The compounds of the present invention are especially active against *Staphylococcus aureus*, including resistant *Staphylococcus aureus* such as for example methicillin resistant *Staphylococcus aureus* (MRSA), and *Streptococcus pneumoniae*.

In particular, the compounds of the present invention are active on those bacteria of which the viability depends on proper functioning of F1F0 ATP synthase. Without being bound to any theory, it is taught that the activity of the present compounds lies in inhibition of the F1F0 ATP synthase, in particular the inhibition of the F0 complex of the F1F0 ATP synthase, more in particular the inhibition of subunit c of the F0 complex of the F1F0 ATP synthase, leading to killing of the bacteria by depletion of the cellular ATP levels of the bacteria.

Whenever used hereinbefore or hereinafter, that the compounds can treat a bacterial infection it is meant that the compounds can treat an infection with one or more bacterial strains.

Whenever used hereinbefore or hereinafter, that the bacterial infection is other than a Mycobacterial infection it is meant that the bacterial infection is other than an infection with one or more *Mycobacteria* strains.

The exact dosage and frequency of administration of the present compounds depends on the particular compound of Formula (Ia) or (Ib) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention.

The compound of the present invention may be administered in a pharmaceutically acceptable form optionally in a pharmaceutically acceptable carrier. The compounds and compositions comprising the compounds can be administered by routes such as topically, locally or systemically. Systemic application includes any method of introducing the compound into the tissues of the body, e.g., intrathecal, epidural, intramuscular, transdermal, intravenous, intraperitoneal, subcutaneous, sublingual, rectal, and oral administration. The specific dosage of antibacterial to be administered, as well as the duration of treatment, may be adjusted as needed.

Bacterial infections which may be treated by the present compounds include, for example, central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients.

Given the fact that the compounds of Formula (Ia) or (Ib) are active against bacterial infections, the present compounds may be combined with other antibacterial agents in order to effectively combat bacterial infections.

Therefore, the present invention also relates to a combination of (a) a compound of Formula (Ia) or (Ib), and (b) one or more other antibacterial agents provided that the one or more other antibacterial agents are other than antimycobacterial agents.

The present invention also relates to a combination of (a) a compound of Formula (Ia) or (Ib), and (b) one or more other antibacterial agents provided that the one or more other antibacterial agents are other than antimycobacterial agents, for use as a medicine.

A pharmaceutical composition comprising a pharmaceutically acceptable carrier and, as active ingredient, a therapeutically effective amount of (a) a compound of Formula (Ia) or (Ib), and (b) one or more other antibacterial agents provided that the one or more other antibacterial agents are other than antimycobacterial agents, is also comprised by the present invention.

The present invention also relates to the use of a combination or pharmaceutical composition as defined above for the treatment of a bacterial infection.

The present pharmaceutical composition may have various pharmaceutical forms for administration purposes. As appropriate compositions there may be cited all compositions usually employed for systemically administering drugs. To prepare the pharmaceutical compositions of this invention, an effective amount of the particular compounds, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral unit dosage forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations.

Depending on the mode of administration, the pharmaceutical composition will preferably comprise from 0.05 to 99% by weight, more preferably from 0.1 to 70% by weight of the active ingredients, and, from 1 to 99.95% by weight, more preferably from 30 to 99.9 weight % of a pharmaceutically acceptable carrier, all percentages being based on the total composition.

The weight to weight ratio's of the compound of Formula (Ia) or (Ib) and (b) the other antibacterial agent(s) when given as a combination may be determined by the person skilled in the art. Said ratio and the exact dosage and frequency of administration depends on the particular compound of Formula (Ia) or (Ib) and the other antibacterial agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention.

The compounds of Formula (Ia) or (Ib) and the one or more other antibacterial agents may be combined in a single preparation or they may be formulated in separate preparations so that they can be administered simultaneously, separately or sequentially. Thus, the present invention also relates to a product containing (a) a compound of Formula (Ia) or (Ib), and (b) one or more other antibacterial agents provided that the one or more other antibacterial agents are other than antimycobacterial agents, as a combined preparation for simultaneous, separate or sequential use in the treatment of a bacterial infection.

The pharmaceutical composition may additionally contain various other ingredients known in the art, for example, a lubricant, stabilising agent, buffering agent, emulsifying agent, viscosity-regulating agent, surfactant, preservative, flavouring or colorant.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof. The daily dosage of the compound according to the invention will, of course, vary with the compound employed, the mode of administration, the treatment desired and the bacterial disease indicated.

The other antibacterial agents which may be combined with the compounds of Formula (Ia) or (Ib) are antibacterial agents known in the art. The other antibacterial agents comprise antibiotics of the β-lactam group such as natural penicillins, semisynthetic penicillins, natural cephalosporins, semisynthetic cephalosporins, cephamycins, 1-oxacephems, clavulanic acids, penems, carbapenems, nocardicins, monobactams; tetracyclines, anhydrotetracyclines, anthracyclines; aminoglycosides; nucleosides such as N-nucleosides, C-nucleosides, carbocyclic nucleosides, blasticidin S; macrolides such as 12-membered ring macrolides, 14-membered ring macrolides, 16-membered ring macrolides; ansamycins; peptides such as bleomycins, gramicidins, polymyxins, bacitracins, large ring peptide antibiotics containing lactone linkages, actinomycins, amphomycin, capreomycin, distamycin, enduracidins, mikamycin, neocarzinostatin, stendomycin, viomycin, virginiamycin; cycloheximide; cycloserine; variotin; sarkomycin A; novobiocin; griseofulvin; chloramphenicol; mitomycins; fumagillin; monensins; pyrrolnitrin; fosfomycin; fusidic acid; D-(p-hydroxyphenyl)glycine; D-phenylglycine; enediynes.

Specific antibiotics which may be combined with the present compounds of Formula (Ia) or (Ib) are for example benzylpenicillin (potassium, procaine, benzathine), phenoxymethylpenicillin (potassium), phenethicillin potassium, propicillin, carbenicillin (disodium, phenyl sodium, indanyl sodium), sulbenicillin, ticarcillin disodium, methicillin sodium, oxacillin sodium, cloxacillin sodium, dicloxacillin, flucloxacillin, ampicillin, mezlocillin, piperacillin sodium, amoxicillin, ciclacillin, hectacillin, sulbactam sodium, talampicillin hydrochloride, bacampicillin hydrochloride, pivmecillinam, cephalexin, cefaclor, cephaloglycin, cefadroxil, cephradine, cefroxadine, cephapirin sodium, cephalothin sodium, cephacetrile sodium, cefsulodin sodium, cephaloridine, cefatrizine, cefoperazone sodium, cefamandole, vefotiam hydrochloride, cefazolin sodium, ceftizoxime sodium, cefotaxime sodium, cefmenoxime hydrochloride, cefuroxime, ceftriaxone sodium, ceftazidime, cefoxitin, cefmetazole, cefotetan, latamoxef, clavulanic acid, imipenem, aztreonam, tetracycline, chlortetracycline hydrochloride, demethylchlortetracycline, oxytetracycline, methacycline, doxycycline, rolitetracycline, minocycline, daunorubicin hydrochloride, doxorubicin, aclarubicin, kanamycin sulfate, bekanamycin, tobramycin, gentamycin sulfate, dibekacin, amikacin, micronomicin, ribostamycin, neomycin sulfate, paromomycin sulfate, streptomycin sulfate, dihydrostreptomycin, destomycin A, hygromycin B, apramycin, sisomicin, netilmicin sulfate, spectinomycin hydrochloride, astromicin sulfate, validamycin, kasugamycin, polyoxin, blasticidin S, erythromycin, erythromycin estolate, oleandomycin phosphate, tracetyloleandomycin, kitasamycin, josamycin, spiramycin, tylosin, ivermectin, midecamycin, bleomycin sulfate, peplomycin sulfate, gramicidin S, polymyxin B, bacitracin, colistin sulfate, colistinmethanesulfonate sodium, enramycin, mikamycin, virginiamycin, capreomycin sulfate, viomycin, enviomycin, vancomycin, actinomycin D, neocarzinostatin, bestatin, pepstatin, monensin, lasalocid, salinomycin, amphotericin B, nystatin, natamycin, trichomycin, mithramycin, lincomycin, clindamycin, clindamycin palmitate hydrochloride, flavophospholipol, cycloserine, pecilocin, griseofulvin, chloramphenicol, chloramphenicol palmitate, mitomycin C, pyrrolnitrin, fosfomycin, fusidic acid, bicozamycin, tiamulin, siccanin.

GENERAL PREPARATION

The compounds according to the invention can generally be prepared by a succession of steps, each of which is known to the skilled person.

Compounds of Formula (Ia) and (Ib) wherein Z is $CH_2$, said compounds being represented by Formula (Ia-1) and (Ib-1), can be prepared by reacting an intermediate of formula (II-a) and (II-b) with paraformaldehyde in a suitable solvent, such as for example toluene.

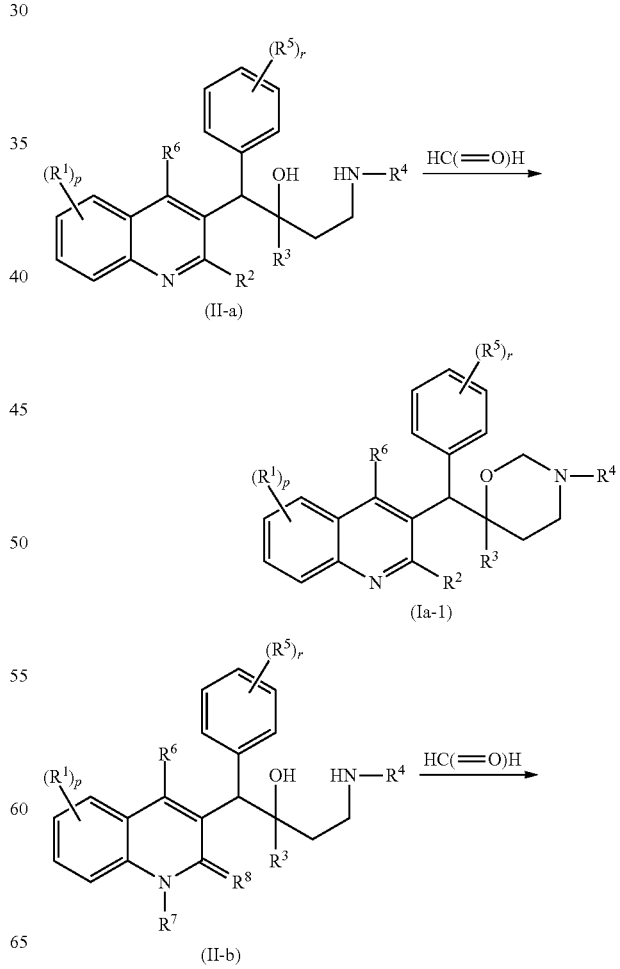

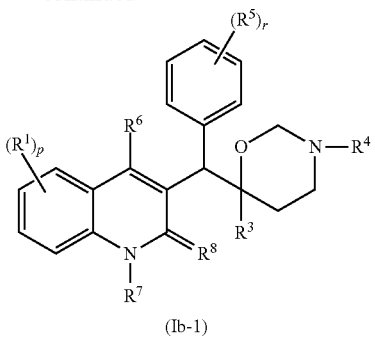

(Ib-1)

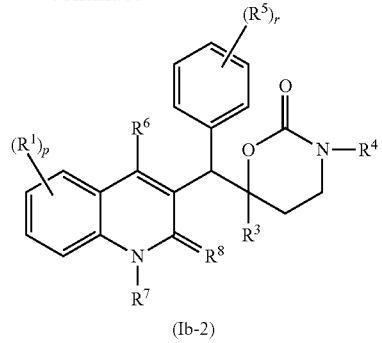

(Ib-2)

Compounds of Formula (Ia) and (Ib) wherein Z is C(=O), said compounds being represented by Formula (Ia-2) and (Ib-2), can be prepared by reacting an intermediate of formula (III-a) and (III-b) wherein $W_1$ represents a suitable leaving group, such as for example imidazole, alkoxy groups, e.g. methoxy, with a suitable base, such as for example sodium hydride, potassium tertiobutylate, in a suitable solvent, such as for example tetrahydrofuran, diethylether, dioxane.

(III-a)

(Ia-2)

(III-b)

In the above reactions, the obtained compound of Formula (Ia) or (Ib) can be isolated, and, if necessary, purified according to methodologies generally known in the art such as, for example, extraction, crystallization, distillation, trituration and chromatography. In case the compound of Formula (Ia) or (Ib) crystallizes out, it can be isolated by filtration. Otherwise, crystallization can be caused by the addition of an appropriate solvent, such as for example water; acetonitrile; an alcohol, such as for example methanol, ethanol; and combinations of said solvents. Alternatively, the reaction mixture can also be evaporated to dryness, followed by purification of the residue by chromatography (e.g. reverse phase HPLC, flash chromatography and the like). The reaction mixture can also be purified by chromatography without previously evaporating the solvent. The compound of Formula (Ia) or (Ib) can also be isolated by evaporation of the solvent followed by recrystallisation in an appropriate solvent, such as for example water; acetonitrile; an alcohol, such as for example methanol; and combinations of said solvents.

The person skilled in the art will recognise which method should be used, which solvent is the most appropriate to use or it belongs to routine experimentation to find the most suitable isolation method.

The compounds of Formula (Ia) or (Ib) may further be prepared by converting compounds of Formula (Ia) or (Ib) into each other according to art-known group transformation reactions.

The compounds of Formula (Ia) or (Ib) may be converted to the corresponding N-oxide forms following art-known procedures for converting a trivalent nitrogen into its N-oxide form. Said N-oxidation reaction may generally be carried out by reacting the starting material of Formula (Ia) or (Ib) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of Formula (Ia) or (Ib) wherein $R^4$ is alkyl, may be converted into a suitable quaternary amine by reaction with a suitable quaternizing agent, such as, for example, an optionally substituted alkylhalide, e.g. $ICH_3$ or $ICH_2CH_3$ in the presence of a suitable solvent, such as for example acetone.

Some of the compounds of Formula (Ia) or (Ib) and some of the intermediates in the present invention may consist of a mixture of stereochemically isomeric forms. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of Formula (Ia) or (Ib) and intermediates involves liquid chromatography, in particular liquid chromatography using a chiral stationary phase.

It is to be understood that in the above or the following preparations, the reaction products may be isolated from the reaction medium and, if necessary, further purified according to methodologies generally known in the art such as, for example, extraction, crystallization, distillation, trituration and chromatography.

Some of the intermediates and starting materials are known compounds and may be commercially available or may be prepared according to art-known procedures or procedures described in WO2004/011436, which is incorporated herein by reference.

Intermediates of formula (II-a) and (II-b) can be prepared by reacting an intermediate of formula (IV-a) and (IV-b) with a suitable deprotecting agent, such as for example 1-chloroethyl chloroformate, in a suitable solvent, such as for example 1,2-dichloroethane and a suitable alcohol, such as for example methanol and the like.

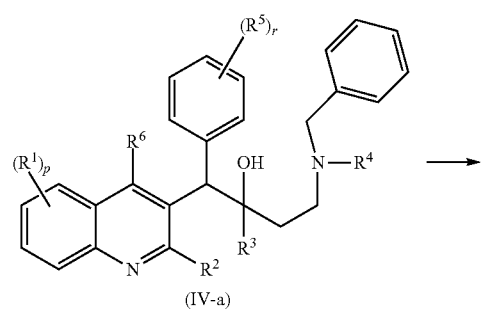

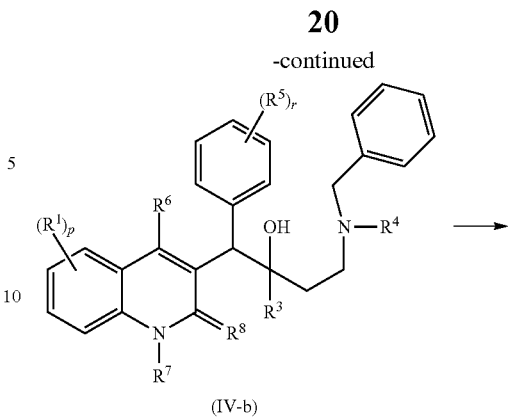

Intermediates of formula (II-a) or (II-b) can also be prepared by reacting an intermediate of formula (IV-a) or (IV-b) with ammonium formate in the presence of palladium on charcoal and in the presence of a suitable solvent, such as for example an alcohol, e.g. methanol. Intermediates of formula (IV-a) or (IV-b) wherein $R^1$ is halo, may loose said halo substituent during their transformation to intermediates of formula (II-a) or (II-b).

Intermediates of formula (IV-a) and (IV-b) can be prepared by reacting an intermediate of formula (V-a) and (V-b) with an intermediate of formula (VI) in the presence of a suitable reducing agent, such as for example n-BuLi, in the presence of a suitable base, such as for example N,N-diisopropylamine, and in the presence of a suitable solvent, such as for example tetrahydrofuran.

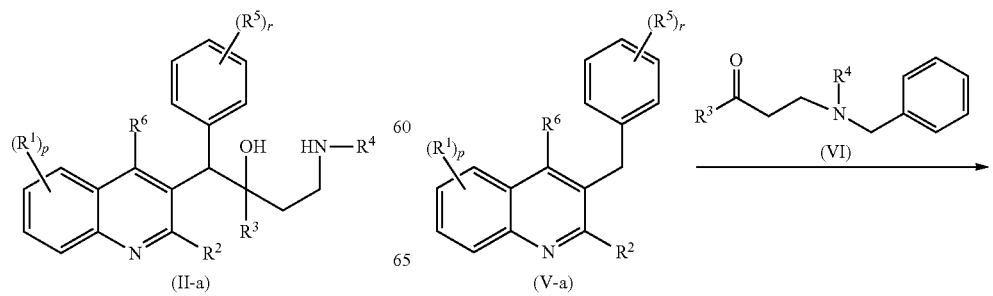

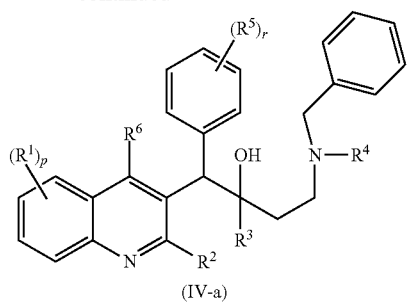

(IV-a)

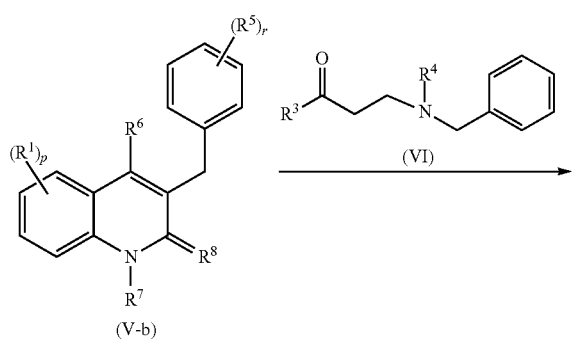

(V-b) → (VI) →

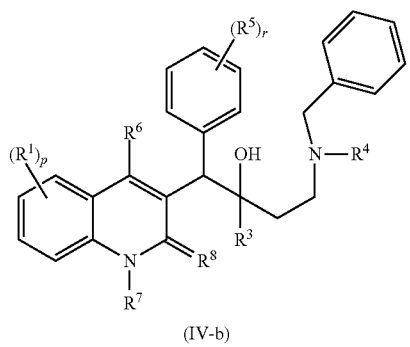

(IV-b)

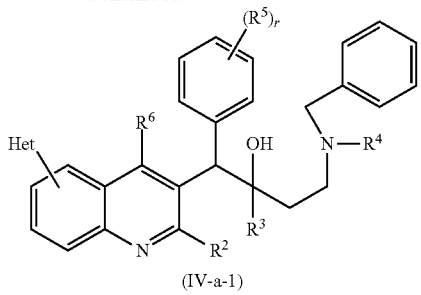

(IV-a-1)

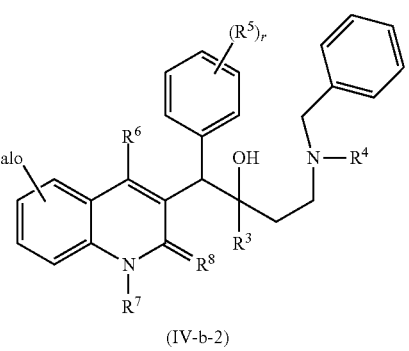

(IV-b-2) → Het-B(OH)₂ (VII) →

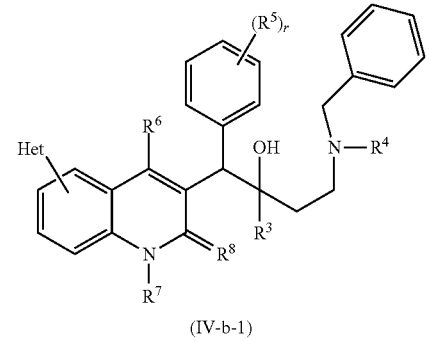

(IV-b-1)

Intermediates of formula (IV-a) or (IV-b) wherein $R^1$ represents Het and p is 1, said intermediates being represented by formula (IV-a-1) or (IV-b-1), can be prepared by reacting an intermediate of formula (IV-a) or (IV-b) wherein $R^1$ represents halo, said intermediates being represented by formula (IV-a-2) or (IV-b-2), with an intermediate of formula (VII) in the presence of a suitable catalyst, such as for example Pd(PPh₃)₄, a suitable base, such as for example K₂CO₃, and a suitable solvent, such as for example dimethylether and a suitable alcohol, such as for example methanol and the like.

Intermediates of formula (III-a) or (III-b) can be prepared by reacting an intermediate of formula (II-a) or (II-b) with an intermediate of formula (VIII) wherein $W_1$—(C═O) represents the group that has to be introduced and R represents the remaining of the intermediate, such as for example 1, 1'-carbonylbis-1H-imidazole, methylchloroformiate or ethylchloroformiate, in the presence of a suitable solvent, such as for example tetrahydrofuran.

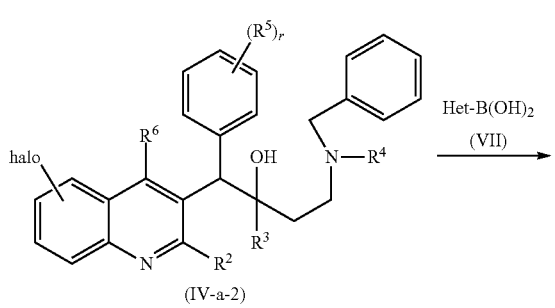

(IV-a-2) → Het-B(OH)₂ (VII) →

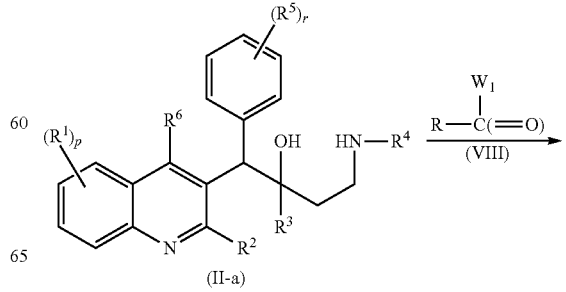

(II-a) → $R-C(=O)$ (VIII) →

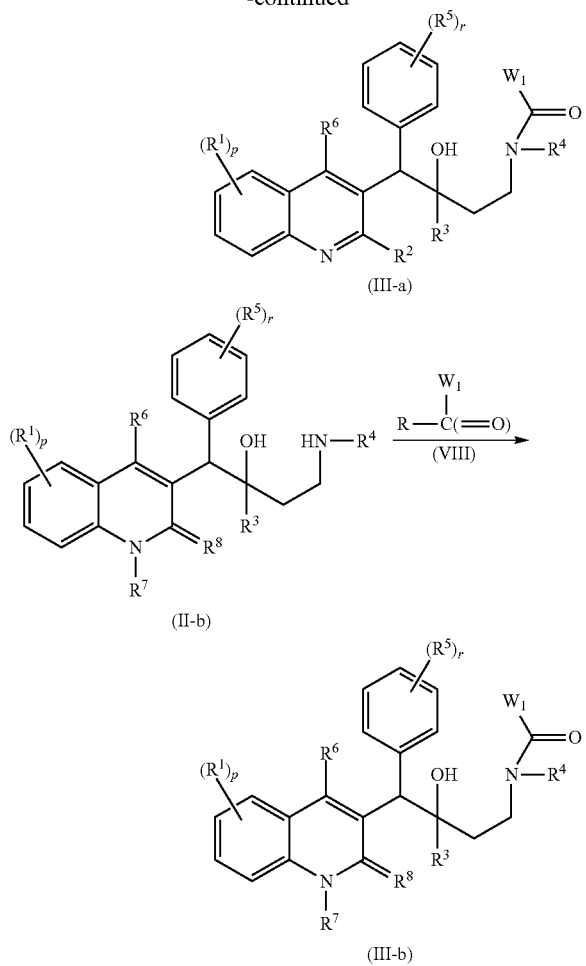

The intermediate compounds of formula (V-a) or (V-b) are compounds that are either commercially available or may be prepared according to conventional reaction procedures generally known in the art. For example, intermediates of formula (V-a-1) may be prepared according to the following reaction scheme (1):

wherein all variables are defined as in Formula (Ia) and (Ib). Reaction scheme (1) comprises step (a) in which an appropriately substituted aniline is reacted with an appropriate acylchloride such as 3-phenylpropionyl chloride, 3-fluorobenzenepropionyl chloride or p-chlorobenzenepropionyl chloride, in the presence of a suitable base, such as triethylamine and a suitable reaction-inert solvent, such as methylene chloride or ethylene dichloride. The reaction may conveniently be carried out at a temperature ranging between room temperature and reflux temperature. In a next step (b) the adduct obtained in step (a) is reacted with phosphoryl chloride ($POCl_3$) in the presence of a suitable solvent, such as for example N,N-dimethylformamide (Vilsmeier-Haack formylation followed by cyclization). The reaction may conveniently be carried out at a temperature ranging between room temperature and reflux temperature. In a next step (c) a specific $R^2$-group, wherein $R^2$ is an alkyloxy or alkylthio radical is introduced by reacting the intermediate compound obtained in step (b) with a compound —X-Alk, wherein X=S or O and Alk is an alkylgroup as defined in Formula (Ia) and (Ib), such as for example sodium methanolate, in the presence of a suitable solvent, such as for example an alcohol, e.g. methanol.

Intermediates according to formula (V-a-2) may be prepared according to the following reaction scheme (2), wherein in a first step (a) a substituted indole-2,3-dione is reacted with a substituted 3-phenylpropionaldehyde in the presence of a suitable base such as sodium hydroxide (Pfitzinger reaction), after which the carboxylic acid compound in a next step (b) is decarboxylated at high temperature in the presence of a suitable reaction-inert solvent such as diphenylether.

Scheme 2

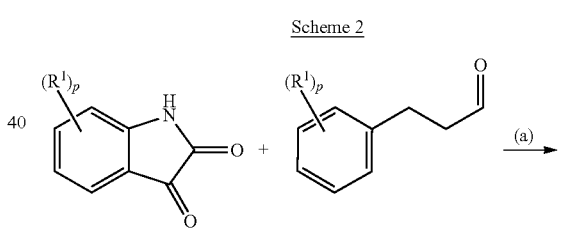

Scheme 1

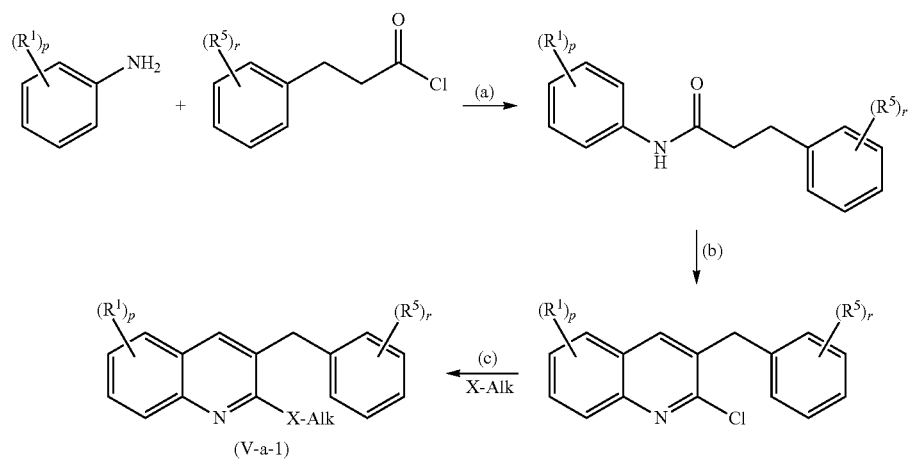

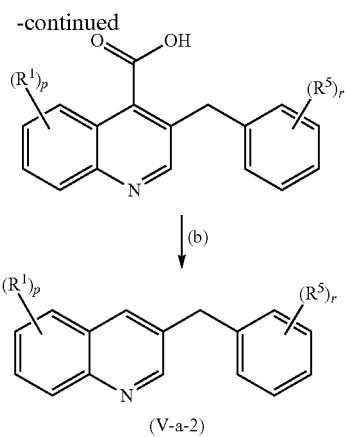

(V-a-2)

It is evident that in the foregoing and in the following reactions, the reaction products may be isolated from the reaction medium and, if necessary, further purified according to methodologies generally known in the art, such as extraction, crystallization and chromatography. It is further evident that reaction products that exist in more than one enantiomeric form, may be isolated from their mixture by known techniques, in particular preparative chromatography, such as preparative HPLC, chiral chromatography. Individual diastereoisomers or individual enantiomers can also be obtained by Supercritical Fluid Chromatography (SCF).

The intermediates of formula (VI) are compounds that are either commercially available or may be prepared according to conventional reaction procedures generally known in the art. For example, intermediate compounds of formula (VI) may be prepared according to the following reaction scheme (3):

Scheme 3

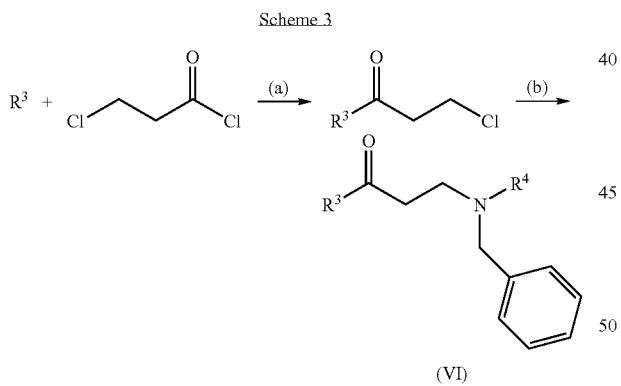

(VI)

Reaction scheme (3) comprises step (a) in which $R^3$, for example an appropriately substituted phenyl, naphthyl, or Het, is reacted by Friedel-Craft reaction with an appropriate acylchloride such as 3-chloropropionyl chloride or 4-chlorobutyryl chloride, in the presence of a suitable Lewis acid, such as $AlCl_3$, $FeCl_3$, $SnCl_4$, $TiCl_4$ or $ZnCl_2$ and optionally a suitable reaction-inert solvent, such as methylene chloride or ethylene dichloride. The reaction may conveniently be carried out at a temperature ranging between room temperature and reflux temperature. In a next step (b) an amino group ($-NR_4(CH_2-C_6H_5)$) is introduced by reacting the intermediate compound obtained in step (a) with a primary or secondary amine, in the presence of a suitable solvent, such as for example acetonitrile, and optionally in the presence of a suitable base, such as for example $K_2CO_3$.

The following examples illustrate the present invention without being limited thereto.

EXPERIMENTAL PART

Of some compounds the absolute stereochemical configuration of the stereogenic carbon atom(s) therein was not experimentally determined. In those cases the stereochemically isomeric form which was first isolated is designated as "A" and the second as "B", without further reference to the actual stereochemical configuration. However, said "A" and "B" isomeric forms can be unambiguously characterized by a person skilled in the art, using art-known methods such as, for example, X-ray diffraction.

In case "A" and "B" are stereoisomeric mixtures, in particular mixtures of diastereoisomers, they can be further separated whereby the respective first fractions isolated are designated "A1" respectively "B1" and the second as "A2" respectively "B2", without further reference to the actual stereochemical configuration. However, said "A1", "A2" and "B1", "B2" isomeric forms, in particular said "A1", "A2" and "B1", "B2" enantiomeric forms, can be unambiguously characterized by a person skilled in the art, using art-known methods such as, for example, X-ray diffraction.

For the synthesis of the present compounds, reference is made to WO2005/070924, which is incorporated herein by reference.

Hereinbelow, Rt means retention time (in minutes) as obtained in the LCMS analysis.

Experimental Part

Hereinafter, the term 'M.P.' means melting point, 'THF' means tetrahydrofuran, 'EtOAc' means ethyl acetate, 'MeOH' means methanol, 'DME' means dimethyl ether, 'DIPE' means diusopropyl ether, 'DMF' means N,N-dimethylformamide, 'Et$_3$N' means triethylamine, 'Pd(PPh$_3$)$_4$' means tetrakis(triphenylphosphine)palladium, 'CDI' means 1,1'-carbonylbis-1H-imidazole.

A. Preparation of the Intermediates

Example A1

Preparation of Intermediate 1

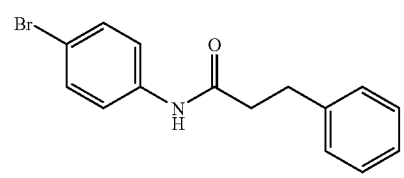

Intermediate 1

Benzenepropanoylchloride (0.488 mol) was added dropwise at room temperature to a solution of 4-bromobenzenamine (0.407 mol) in Et$_3$N (70 ml) and CH$_2$Cl$_2$ (700 ml) and into water and concentrated NH$_4$OH, and extracted with CH$_2$Cl$_2$. The organic layer was dried (MgSO$_4$), filtered, and the solvent was evaporated. The residue was crystallized from diethyl ether. The residue (119.67 g) was taken up in CH$_2$Cl$_2$ and washed with HCl 1N. The organic layer was dried (MgSO$_4$), filtered, and the solvent was evaporated. Yield: 107.67 g of intermediate 1.

Example A2

Preparation of Intermediate 2

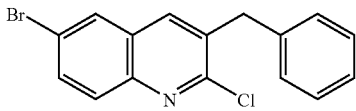

Intermediate 2

The reaction was carried out twice. POCl$_3$ (1.225 mol) was added dropwise at 10° C. to DMF (0.525 mol). Then intermediate 1 (0.175 mol) was added at room temperature. The mixture was stirred overnight at 80° C., poured out on ice and extracted with CH$_2$Cl$_2$. The organic layer was dried (MgSO$_4$), filtered, and the solvent was evaporated, yielding 77.62 g (67%) of intermediate 2. The product was used without further purification.

Example A3

Preparation of Intermediate 3

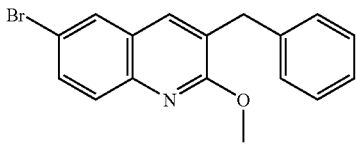

Intermediate 3

A mixture of intermediate 2 (0.233 mol) in CH$_3$ONa (30%) in MeOH (222.32 ml) and MeOH (776 ml) was stirred and refluxed overnight, then poured out on ice and extracted with CH$_2$Cl$_2$. The organic layer was separated, dried (MgSO$_4$), filtered and the solvent was evaporated. The residue was purified by column chromatography over silica gel (eluent: CH$_2$Cl$_2$/cyclohexane 20/80 and then 100/0; 20-45 μm). The pure fractions were collected and the solvent was evaporated. Yield: 25 g (33%) of intermediate 3 (M.P.: 84° C.).

Example A4 a) Preparation of Intermediates 4 and 5

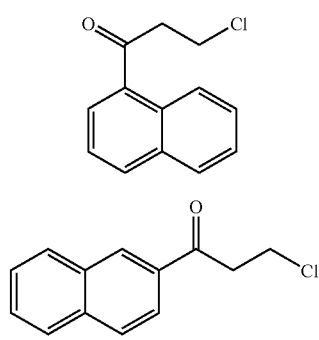

Intermediate 4

Intermediate 5

A mixture of aluminium chloride (34.3 g, 0.257 mol) and 3-chloropropanoyl chloride (29.7 g, 0.234 mol) in 1,2-dichloroethane (150 ml) was stirred at 0° C. A solution of naphthalene (30 g, 0.234 mol) in 1,2-dichloroethane (50 ml) was added. The mixture was stirred at 5° C. for 2 hours and poured out into ice water. The organic layer was separated, dried (MgSO$_4$), filtered, and the solvent was evaporated. The residue (56 g) was purified by column chromatography over silica gel (eluent: cyclohexane/CH$_2$Cl$_2$: 60/40; 20-45 μm). Two fractions were collected and the solvent was evaporated to afford intermediate 4 (31 g, 61%) as an oil. The second fraction (14 g) was taken up in DIPE to afford intermediate 5 (8.2 g, 16%; M.P.: 68° C.) as a pale yellow solid.

Following intermediate was prepared according to the previous procedure:

| Intermediate 41 | The residue (20.0 g) was used for the next step without further purification. | 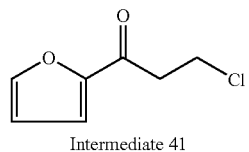 |
|---|---|---|

Intermediate 41 b) Preparation of Intermediate 6

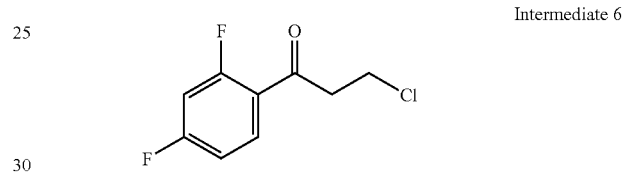

Intermediate 6

Aluminum chloride (0.3 mol) was added carefully to 1,3-difluorobenzene (0.26 mol) and they were heated with vigorously stirring till 50° C. 3-chloropropanoyl chloride (0.26 mol) was added dropwise over a 15 minute period at 40° C. (cooled on ice) and the mixture was stirred at 50° C. The mixture was poured into water (250 ml), ice (250 g) and HCl (25 ml) and it was stirred for 20 minutes. The formed precipitate was filtered off and extracted with CH$_2$Cl$_2$ and water. Yield: 40 g of intermediate 6 (75%).

Example A5 a) Preparation of Intermediate 7

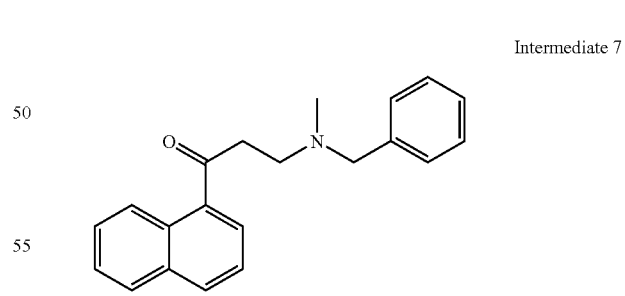

Intermediate 7

A mixture of intermediate 4 (3 g; 0.0137 mol), N-benzylmethyl amine (2 ml; 0.0150 mol) in acetonitrile (100 ml) was stirred at 80° C. for 2 hours. At room temperature water was added. The mixture was extracted with CH$_2$Cl$_2$. The organic layer was separated and dried (MgSO$_4$), filtered, and the solvent was evaporated. The residue (6 g) was purified by column chromatography over silica gel (eluent: CH$_2$Cl$_2$/MeOH: 97/3; 20-45 μm) to afford an oil. Yield: 4.2 g of intermediate 7.

Following intermediate was prepared according to the previous procedure:

| Intermediate 42 | The residue (22.5 g) was purified by column chromatography over silica gel (eluent: CH₂Cl₂/MeOH: 98/2; 20-45 μm) to afford an oil. Yield: 5.1 g of intermediate 42 (17%). | 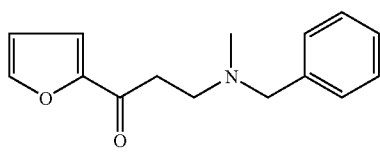<br>Intermediate 42 |
|---|---|---| b) Preparation of Intermediate 8

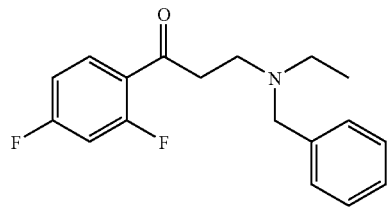

Intermediate 8

A mixture of intermediate 6 (0.015 mol), N-ethylbenzenemethanamine (0.016 mol) and K₂CO₃ (0.016 mol) in acetonitrile (30 ml) was stirred at 70° C. for 2 hours, poured out into H₂O and extracted with CH₂Cl₂. The organic layer was separated, dried (MgSO₄), filtered, and the solvent was evaporated. Yield: 4 g of intermediate 8 (88%).

Example A6 a) Preparation of Intermediate 9

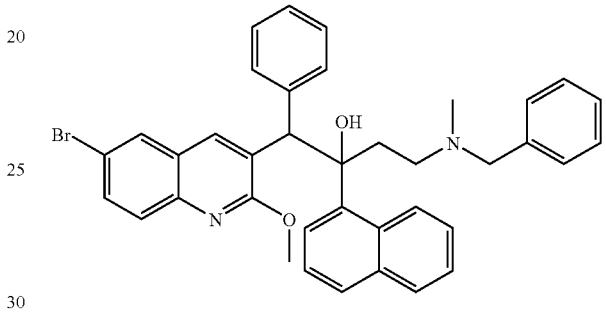

Intermediate 9 n-Butyl lithium (0.0075 mol) was added at 20° C. to a solution of diisopropylamine (0.0075 mol) in THF (50 ml). The mixture was cooled to 70° C. Intermediate 3 (0.0062 mol) was added. The mixture was stirred at 70° C. for 1 hour and 30 minutes. Intermediate 7 (0.0075 mol) was added. The mixture was stirred for 1 hour and 30 minutes. H₂O was added. The mixture was extracted with CH₂Cl₂. The organic layer was separated, dried (MgSO₄), filtered, and the solvent was evaporated. The residue (3 g) was purified by column chromatography over silica gel (eluent: cyclohexane/EtOAc 90/10; 15-40 μm). The pure fractions were collected and the solvent was evaporated. Yield: 1.5 g of a mixture of two diastereoisomers (38%), i.e. intermediate 9.

Following intermediate was prepared according to the previous procedure:

| Intermediate 43 | The residue (7.5 g) was purified by column chromatography over silica gel (eluent: cyclohexane/EtOAc 92/8; 15-40 μm). The pure fractions were collected and the solvent was evaporated. Yield: 3.25 g of intermediate 43 a mixture of two diastereoisomers (55%, mixture of diastereoisomers: 65/35). | 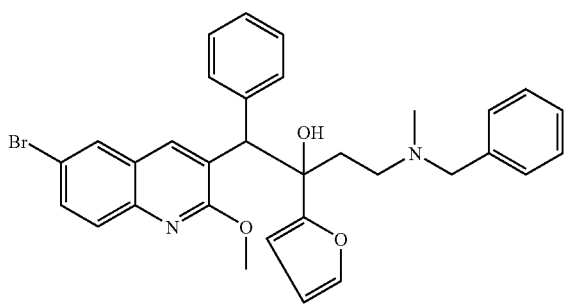<br>Intermediate 43 |
|---|---|---| b) Preparation of Intermediate 10

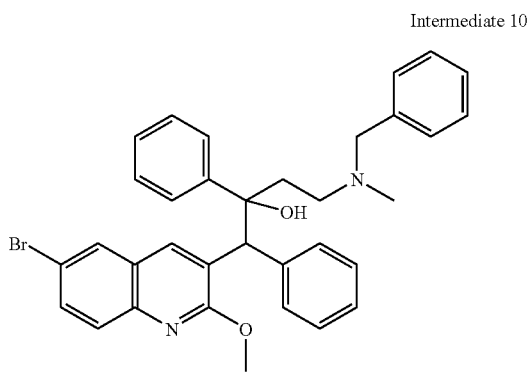 [SMILES: COc1nc2ccc(Br)cc2cc1C(c1ccccc1)C(O)(CCN(C)Cc1ccccc1)c1ccccc1]

Intermediate 10 n-Butyl lithium (0.0075 mol) was added at 20° C. to a solution of diisopropylamine (0.0075 mol) in THF (50 ml). The mixture was cooled to 70° C. Intermediate 3 (0.0061 mol) was added. The mixture was stirred at 70° C. for 1 hour and 30 minutes. 4-[methyl(phenylmethyl)amino]-1-phenyl-1-butanone (0.0073 mol) was added. The mixture was stirred for 1 hour and 30 minutes. H$_2$O was added. The mixture was extracted with CH$_2$Cl$_2$. The organic layer was separated, dried (MgSO$_4$), filtered, and the solvent was evaporated. The residue (4.9 g) was purified by column chromatography over silica gel (eluent: 100% CH$_2$Cl$_2$; 15-40 µm). The pure fractions were collected and the solvent was evaporated, yielding 1.43 g of intermediate 10 (40%, mixture of diastereoisomers: 60/40).

Following intermediates were prepared according to the previous procedure:

| | | |
|---|---|---|
| Intermediate 19 | The residue (6.4 g) was purified by column chromatography over silica gel (eluent: CH$_2$Cl$_2$/cyclohexane 85/15; 15-40 µm). The pure fractions were collected and the solvent was evaporated, yielding 0.81 g of the intermediate as a mixture of diastereoisomers (44/56) (17%). | 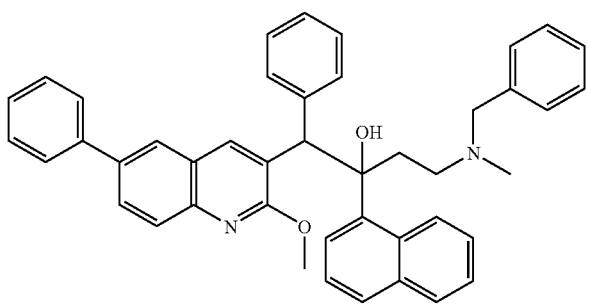<br>Intermediate 19 |
| Intermediate 20 | The residue was purified by column chromatography over silica gel (eluent: cyclohexane/EtOAc 95/5; 15-40 µm). The pure fractions were collected and the solvent was evaporated. Yield: 0.55 g of the intermediate as a mixture of diastereoisomers (12%). | 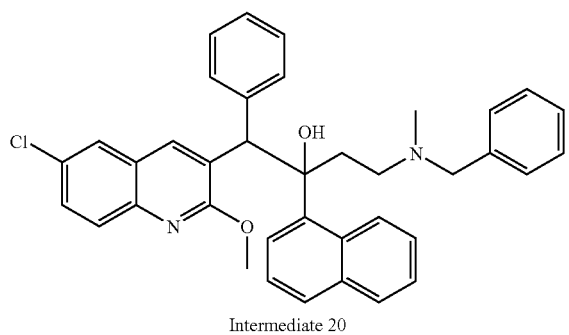 [SMILES: COc1nc2ccc(Cl)cc2cc1C(c1ccccc1)C(O)(CCN(C)Cc1ccccc1)c1cccc2ccccc12]<br>Intermediate 20 |
| Intermediate 21 | The residue was purified by column chromatography over silica gel (eluent: cyclohexane/EtOAc 95/5; 15-40 µm). The pure fractions were collected and the solvent was evaporated, to give 0.34 g of the intermediate as a mixture of diastereoisomers (7%). | 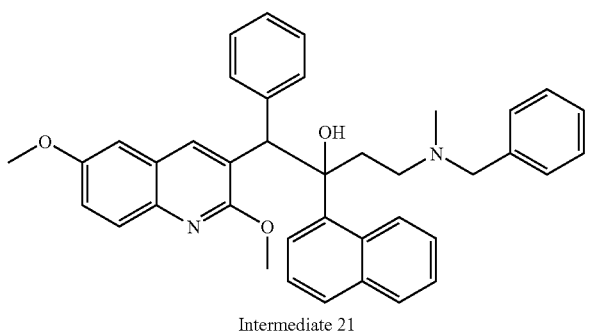 [SMILES: COc1ccc2nc(OC)c(C(c3ccccc3)C(O)(CCN(C)Cc3ccccc3)c3cccc4ccccc34)cc2c1]<br>Intermediate 21 |

| | | |
|---|---|---|
| Intermediate 22 | The residue was purified by column chromatography over silica gel (eluent: cyclohexane/EtOAc 95/5; 15-40 µm). The pure fractions were collected and the solvent was evaporated, yielding 0.80 g of the intermediate as a mixture of diastereoisomers (13%). | 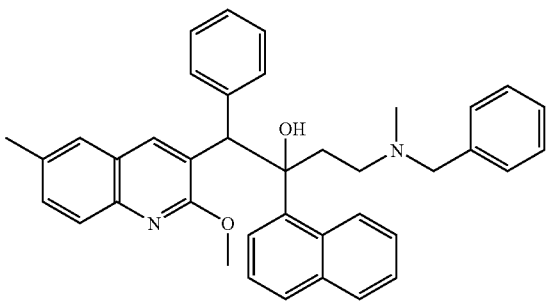<br>Intermediate 22 |
| Intermediate 23 | The residue was purified by column chromatography over silica gel (eluent: cyclohexane/EtOAc 80/20; 15-40 µm). The pure fractions were collected and the solvent was evaporated. The residue (1.3 g) was purified by column chromatography over silica gel (eluent: acetonitrile/NH$_4$CO$_3$ 0.5% 95/5; kromasil). The pure fractions were collected and the solvent was evaporated, affording 0.61 g of the intermediate as a mixture of diastereoisomers (41/59) (18%). | 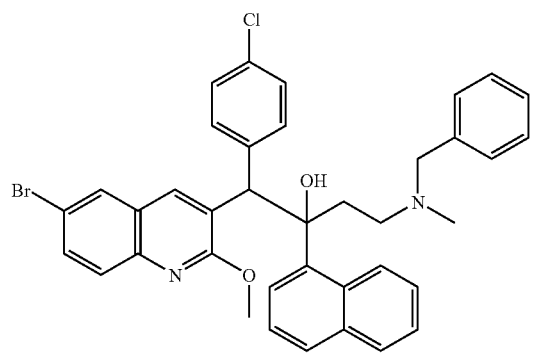<br>Intermediate 23 | c) Preparation of Intermediates 11 and 12

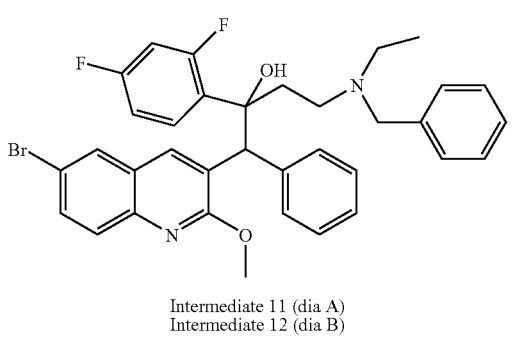 [SMILES: CCN(CCC(O)(c1ccc(F)cc1F)C(c1ccccc1)c1cc2cc(Br)ccc2nc1OC)Cc1ccccc1]

Intermediate 11 (dia A)
Intermediate 12 (dia B)

n-Butyl lithium (0.0075 mol) was added at 20° C. to a solution of diisopropylamine (0.0075 mol) in THF (50 ml). The mixture was cooled to 70° C. Intermediate 3 (0.00824 mol) was added. The mixture was stirred at 70° C. for 1 hour and 30 minutes. Intermediate 8 (0.0099 mol) was added. The mixture was stirred for 1 hour and 30 minutes. H$_2$O was added. The mixture was extracted with CH$_2$Cl$_2$. The organic layer was separated, dried (MgSO$_4$), filtered, and the solvent was evaporated. The residue (5.4 g) was purified by column chromatography over silica gel (eluent: CH$_2$Cl$_2$/cyclohexane 60/40; 15-40 µm). Two fractions were collected and the solvent was evaporated. Yielding: 0.95 g of intermediate 11 as diastereoisomer A (15%, M.P.: 171° C., MH+: 631, Rt: 11.24) and 0.83 g of intermediate 12 as diastereoisomer B (13%, MH+: 631, Rt: 11.17).

Example A7

Preparation of Intermediate 17

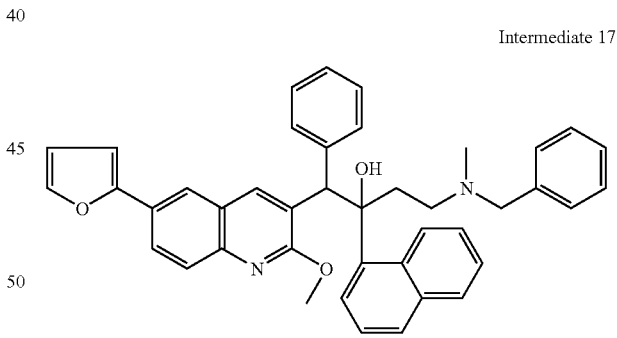

Intermediate 17

Intermediate 9 (1.58 mmol), 2-furanboronic acid (2.69 mmol), Pd(PPh$_3$)$_4$ (0.158 mmol), DME (30 ml), MeOH (10 ml) and K$_2$CO$_3$ (1.6 ml) were heated under microwaves (300 W, 68° C.) for 10 minutes. The mixture was cooled, poured into water and extracted with EtOAc. The organic layer was separated, dried (MgSO$_4$), filtered, and the solvent was evaporated. The residue (1.4 g) was purified by column chromatography over silica gel (eluent: cyclohexane/EtOAc 90/10; 15-40 µm). The pure fractions were collected and the solvent was evaporated. Yield: 0.47 g of intermediate 17 as a mixture of diastereoisomers (60/40) (41%).

Example A8 a-1) Preparation of Intermediates 13 and 14

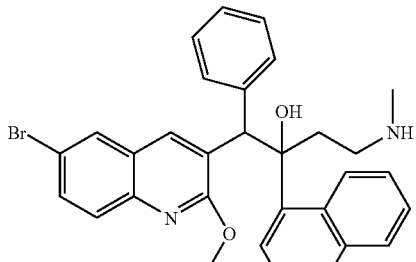

Intermediate 13 (diastereoisomer A)
Intermediate 14 (diastereoisomer B)

1-Chloroethyl chloroformate (15 ml) was added at room temperature to a mixture of intermediate 9 (0.0023 mol) in 1,2-dichloroethane (30 ml). The mixture was stirred at 80° C. for 1 hour. The solvent was evaporated. MeOH (15 ml) was added. The mixture was stirred and refluxed for 30 minutes. The solvent was evaporated. The residue (*) (1.49 g) was purified by column chromatography over silica gel (eluent: $CH_2Cl_2$/MeOH/$NH_4OH$ 97/3/0.1; 15-40 μm). Two fractions were collected and the solvent was evaporated. The first residue (0.23 g) was crystallized from DIPE. The precipitate was filtered off and dried, yielding 0.168 g (13%) of intermediate 13 (diastereoisomer A) (M.P.: 204° C.). The second residue (0.32 g) was crystallized from DIPE. The precipitate was filtered off and dried. Yield: 0.298 g (23%) of intermediate 14 (diastereoisomer B) (M.P.: 225° C.).

Following intermediates were prepared according to the above procedure. The purification of the resulting residue (*) is indicated for each intermediate separately.

| | | |
|---|---|---|
| Intermediate 25 and Intermediate 26 | The residue (1.2 g) was purified by column chromatography over silica gel (eluent: $CH_2Cl_2$/MeOH/$NH_4OH$ 95/5/0.1; 15-40 μm). Two fractions were collected and the solvent was evaporated. Yield: 0.047 g of intermediate 25 (diastereoisomer A) (60%, MH+: 491). The second residue (0.08 g, 10%) was crystallized from DIPE. The precipitate was filtered off and dried. Yield: 0.031 g of intermediate 26 (diastereoisomer B) (4%, M.P.: 197° C.). | 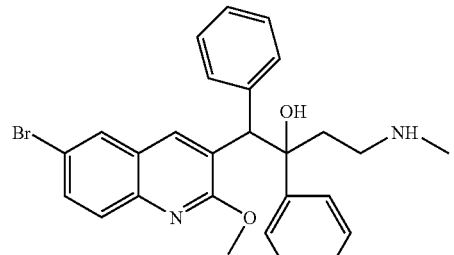 Intermediate 25 (diastereoisomer A) Intermediate 26 (diastereoisomer B) |
| Intermediate 27 and Intermediate 28 | The residue (1.0 g) was purified by column chromatography over silica gel (eluent: $CH_2Cl_2$/MeOH/$NH_4OH$ 96/4/0.1; 15-40 μm). Two fractions were collected and the solvent was evaporated. Yield: 0.105 g of intermediate 27 (diastereoisomer A) (15%, MH+: 539, Rt: 2.48) and 0.11 g of intermediate 28 (diastereoisomer B) (16%, M.P.: 222 ° C.). | 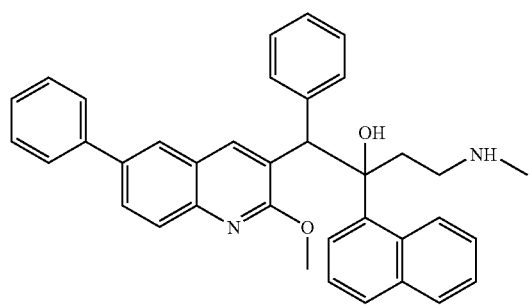 Intermediate 27 (diastereoisomer A) Intermediate 28 (diastereoisomer B) |
| Intermediate 29 and Intermediate 30 | The residue (0.5 g) was purified by column chromatography over silica gel (eluent: $CH_2Cl_2$/MeOH/$NH_4OH$ 97/3/0.1; 10 μm). Two fractions were collected and the solvent was evaporated. Yield: 0.11 g of intermediate 29 (diastereoisomer A) (24%, MH+: 497) and 0.10 g of intermediate 30 (diastereoisomer B) (22%, MH+: 497). | 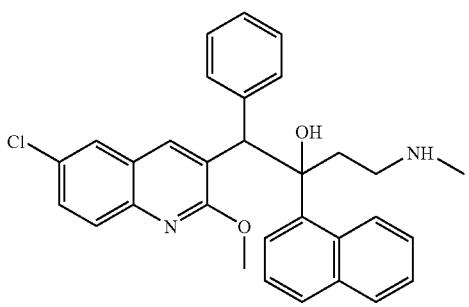 Intermediate 29 (diastereoisomer A) Intermediate 30 (diastereoisomer B) |

| | | |
|---|---|---|
| Intermediate 31 and Intermediate 32 | The residue (0.32 g) was purified by column chromatography over silica gel (eluent: CH₂Cl₂/MeOH/NH₄OH 97/3/0.1; 10 μm). Two fractions were collected and the solvent was evaporated. Yield: 0.10 g of intermediate 31 (diastereoisomer A) (35%, MH+: 493) and 0.04 g of intermediate 32 (diastereoisomer B) (14%, MH+: 493). | 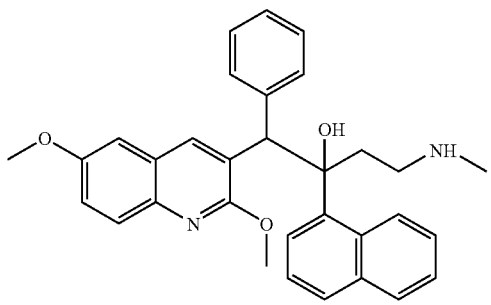<br>Intermediate 31 (diastereoisomer A)<br>Intermediate 32 (diastereoisomer B) |
| Intermediate 33 and Intermediate 34 | The residue (0.9 g) was purified by column chromatography over silica gel (eluent: CH₂Cl₂/MeOH/NH₄OH 98/2/0.1; 10 μm). Two fractions were collected and the solvent was evaporated. Yield: 0.09 g of intermediate 33 (diastereoisomer A) (15%, MH+: 477, Rt: 5.56) and 0.08 g of intermediate 34 (diastereoisomer B) (13%, MH+: 477, Rt: 5.27). | 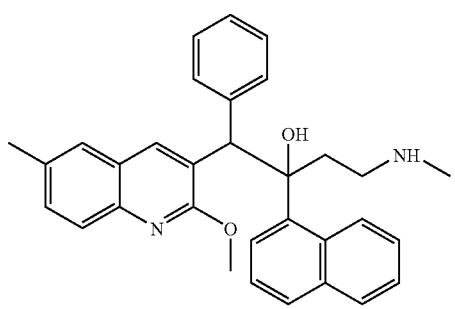<br>Intermediate 33 (diastereoisomer A)<br>Intermediate 34 (diastereoisomer B) |
| Intermediate 35 and Intermediate 36 | The residue (0.45 g) was purified by column chromatography over silica gel (eluent: CH₂Cl₂/MeOH/NH₄OH 96/4/0.1; 10 μm). Two fractions were collected and the solvent was evaporated. Yield: 0.09 g of intermediate 35 (diastereoisomer A) (22%, MH+: 529) and 0.12 g of intermediate 36 (diastereoisomer B) (30%, MH+: 529). | 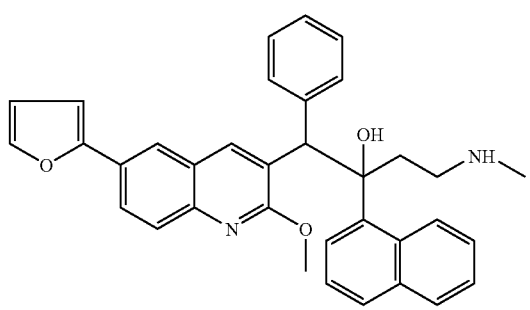<br>Intermediate 35 (diastereoisomer A)<br>Intermediate 36 (diastereoisomer B) |
| Intermediate 37 and Intermediate 38 | The residue (0.63 g) was purified by column chromatography over silica gel (eluent: CH₂Cl₂/MeOH/NH₄OH 98/2/0.1; 15-40 μm). Two fractions were collected and the solvent was evaporated. Yield: 0.08 g of intermediate 37 (diastereoisomer A) (15%, MH+: 575, Rt: 6.70) and 0.06 g of intermediate 38 (diastereoisomer B) (12%, MH+: 575). | 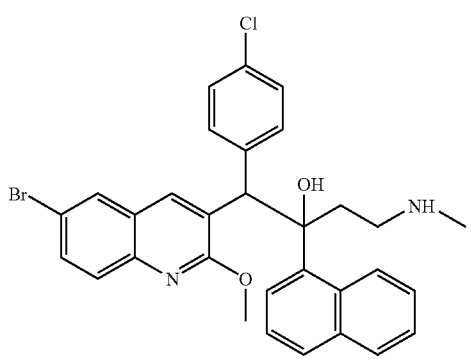<br>Intermediate 37 (diastereoisomer A)<br>Intermediate 38 (diastereoisomer B) |

| | |
|---|---|
| Intermediate 39 | The residue (0.92 g) was purified by column chromatography over silica gel (eluent: CH$_2$Cl$_2$/MeOH 95/5; 15-40 µm). The pure fractions were collected and the solvent was evaporated. Yielding : 0.4 g of intermediate 39 (diastereoisomer A) (56%, MH+: 541). 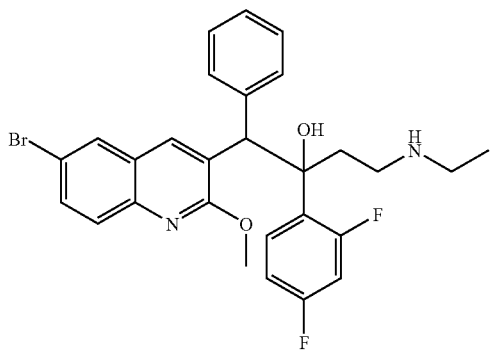<br>Intermediate 39 (diastereoisomer A) |
| Intermediate 40 | The residue (0.49 g) was purified by column chromatography over silica gel (eluent: CH$_2$Cl$_2$/MeOH/NH$_4$OH 96/4/0.1; 15-40 µm). The pure fractions were collected and the solvent was evaporated. Yielding: 0.265 g of intermediate 40 (diastereoisomer B) (66%, MH+: 541). 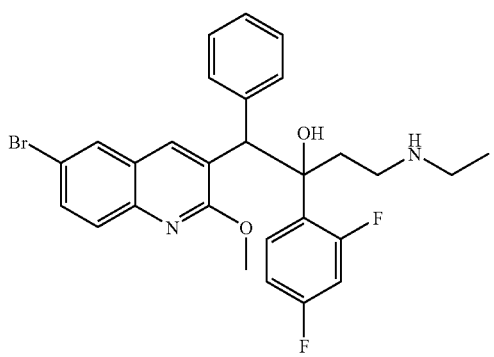<br>Intermediate 40 (diastereoisomer B) | a-2) Preparation of Intermediates 15 and 16

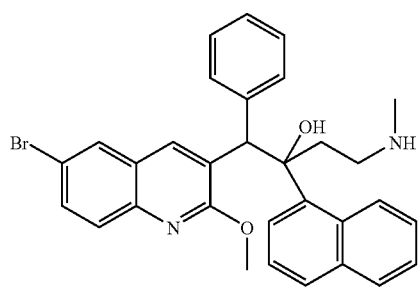

Intermediate 15 (A1)
Intermediate 16 (A2)

Intermediate 13 (diastereoisomer A) (0.9 g) was purified by chiral chromatography over silica gel (eluent:100% ethanol). Two fractions were collected and the solvent was evaporated. Yield: 0.420 g of intermediate 15 (enantiomer A1) (M.P.: 161° C., MH+: 541) and 0.397 g of intermediate 16 (enantiomer A2) (M.P.: 158° C., MH+: 541).

a-3) Preparation of Intermediates 44 and 45

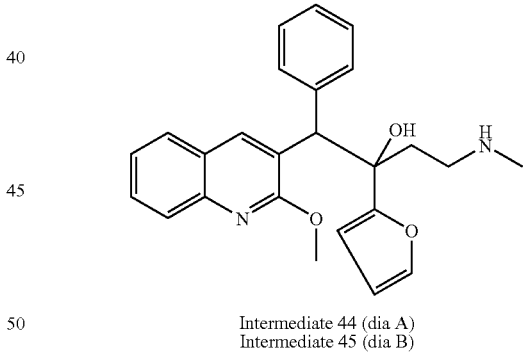

Intermediate 44 (dia A)
Intermediate 45 (dia B)

A mixture of intermediate 43 (prepared according to A6 a) (1.5 g, 2.62 mol), ammonium formate (0.83 g, 0.013 mol) and palladium on charcoal (10%, 1.5 g) in methanol (30 ml) was heated under reflux for 1 hour. The mixture was cooled and filtered on a short pad of celite. Water was added. The organic layer was extracted with ethyl acetate, separated, dried (MgSO$_4$), filtered, and the solvent was evaporated. The residue (1.3 g) was purified by column chromatography over silica gel (eluent: MeOH/AcNH$_4$: 60/40, kromasil C$_{18}$, 5 µm) The pure fractions were collected and the solvent was evaporated yielding two fractions. Yield: 0.14 g of intermediate 44 as diastereoisomer A (12%, MH+: 403) and 0.26 g of intermediate 45 as diastereoisomer B (22%, MH+: 403).

Example A9

Preparation of Intermediate 18

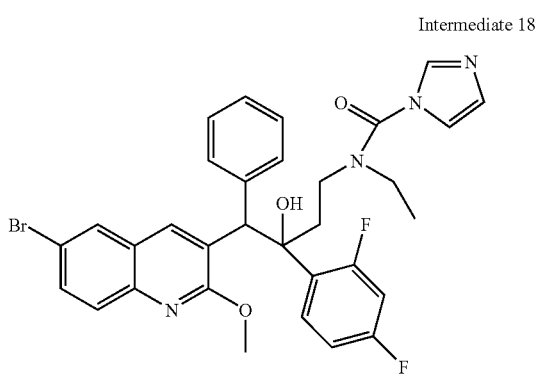 [SMILES: CCN(CCC(O)(c1ccc(F)cc1F)C(c1ccccc1)c1cc2cc(Br)ccc2nc1OC)C(=O)n1ccnc1]

Intermediate 18

A mixture of the intermediate 39 prepared according to example A8.a-1) (0.0002 mol) and CDI (0.0003 mol) in THF (7 ml) was stirred and refluxed for 2 hours, poured out into $H_2O$ and extracted with $CH_2Cl_2$. The organic layer was separated, dried ($MgSO_4$), filtered, and the solvent was evaporated. Yield: 0.15 g of intermediate 18 (diastereoisomer A) (84%).

B. Preparation of the Compounds

Example B1

Preparation of Compound 1

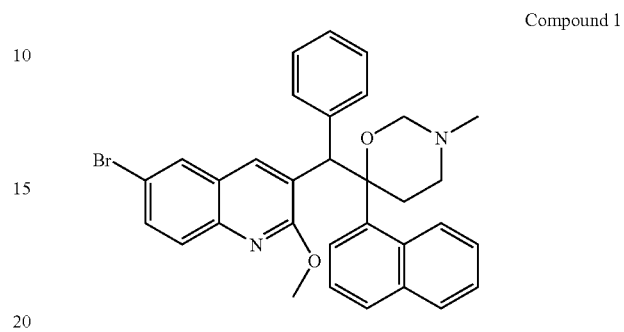

Compound 1

A mixture of intermediate 13 (prepared according to example A8.a-1) (0.00009 mol) and paraformaldehyde (0.0001 mol) in toluene (5 ml) was stirred at 80° C. The mixture was evaporated. The residue (*) was purified by column chromatography over silica gel (eluent:$CH_2Cl_2$/ MeOH 99/1; 15-40 μm). The pure fractions were collected and the solvent was evaporated. Yield: 0.025 g of compound 1 (diastereoisomer A) (49%, M.P.: 112° C.).

Following compounds were prepared according to the above procedure. The purification of the residue (*) is indicated if different from the above-described purification.

| Compound 2 | 0.068 g of diastereoisomer A (69%, MH+: 551, Rt: 4.98) | 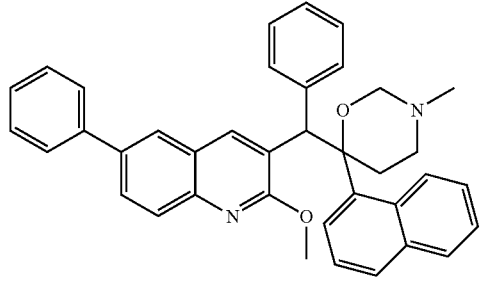 Compound 2 (diastereoisomer A) |
|---|---|---|
| Compound 3 | 0.11 g of diastereoisomer A (98%, MH+: 509, Rt: 6.48) | 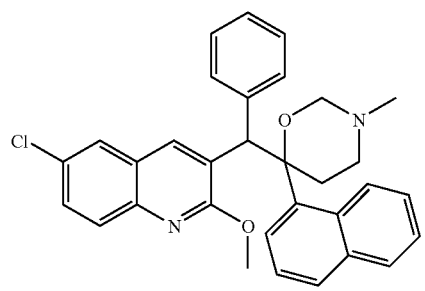 Compound 3 (diastereoisomer A) |

-continued

| | | |
|---|---|---|
| Compound 4 | 0.08 g of diastereoisomer A (80%, MH+: 505, Rt: 5.83) | 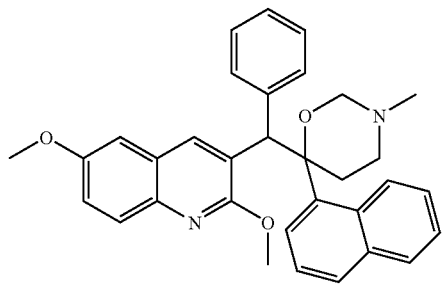<br>Compound 4 (diastereoisomer A) |
| Compound 5 | 0.082 g of diastereoisomer A (100%, MH+: 489, Rt: 3.70) | 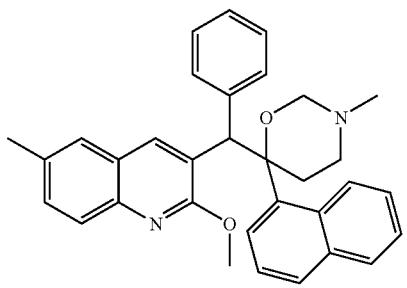<br>Compound 5 (diastereoisomer A) |
| Compound 6 | 0.082 g of diastereoisomer A (89%, MH+: 541, Rt: 4.15) | 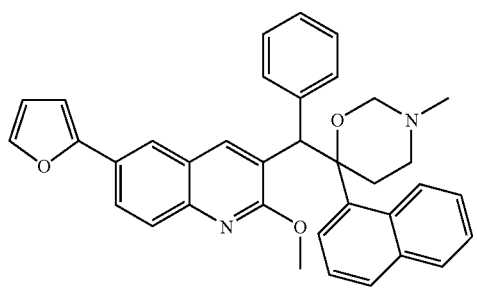<br>Compound 6 (diastereoisomer A) |
| Compound 7 | The residue was purified by column chromatography over silica gel (eluent: CH$_2$Cl$_2$/MeOH 99/1; 15-40 µm). The pure fractions were collected and the solvent was evaporated. Yield: 0.036 g of diastereoisomer B (71%, M.P.: 108° C.). | 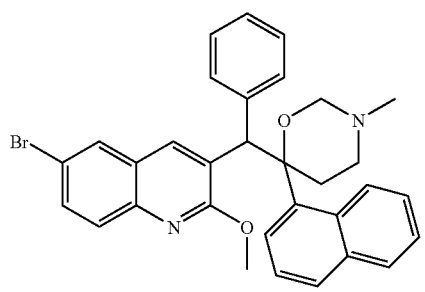<br>Compound 7 (diastereoisomer B) |
| Compound 8 | 0.045 g of diastereoisomer B (88%, M.P.: 168° C.) | 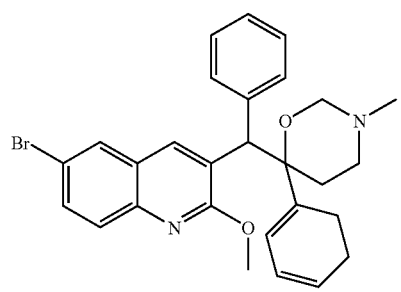<br>Compound 8 (diastereoisomer B) |

| | | |
|---|---|---|
| Compound 9 | 0.077 g of diastereoisomer B (61%, MH+: 551, Rt: 4.65). | 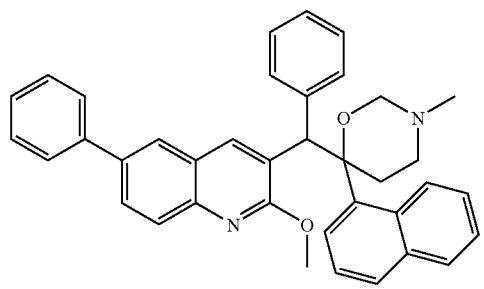<br>Compound 9 (diastereoisomer B) |
| Compound 10 | 0.040 g of diastereoisomer B (100%, MH+: 505, Rt: 5.88). | 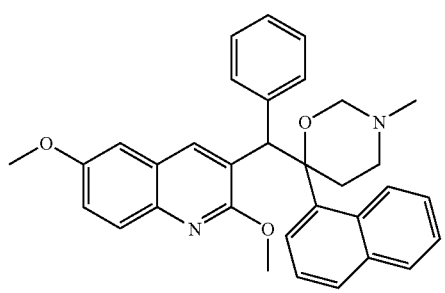<br>Compound 10 (diastereoisomer B) |
| Compound 11 | 0.044 g of diastereoisomer B (72%, MH+: 489, Rt: 3.7). | 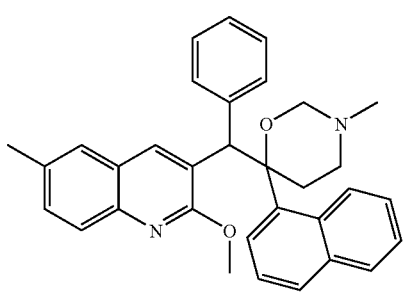<br>Compound 11 (diastereoisomer B) |
| Compound 12 | 0.12 g of diastereoisomer B (98%, MH+: 541, Rt: 3.97). | 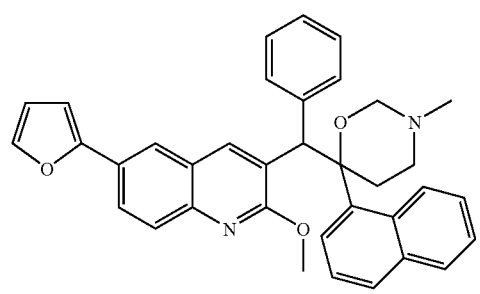<br>Compound 12 (diastereoisomer A) |

-continued

| | | |
|---|---|---|
| Compound 13 | 0.034 g of diastereoisomer B (90%, MH+: 587, Rt: 5.93). | 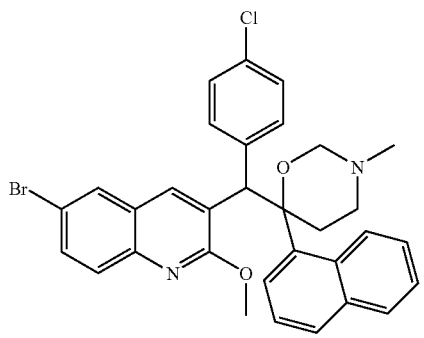<br>Compound 13 (diastereoisomer B) |
| Compound 21 | 0.026 g of diastereoisomer A (40%, M.P. 201° C.). | 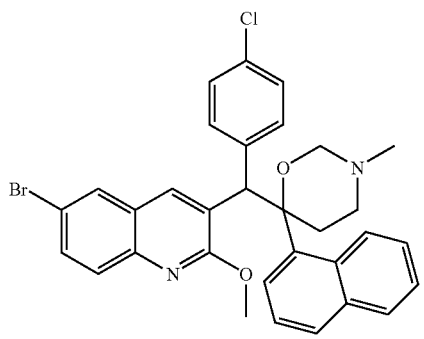<br>Compound 21 (diastereoisomer A) |

Example B2

Preparation of Compound 14

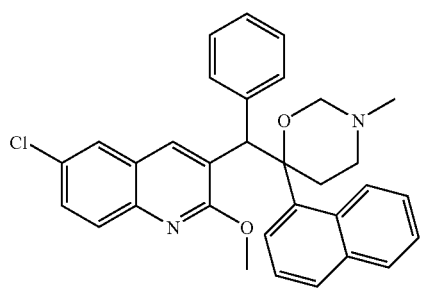

Compound 14

A mixture of intermediate 30 (diastereoisomer B prepared according to example A8.a-1) (0.00009 mol) and paraformaldehyde (0.0001 mol) in toluene (5 ml) was stirred at 80° C. The mixture was evaporated. The residue was purified by column chromatography over silica gel (eluent: CH$_2$Cl$_2$/MeOH 99/1; 15-40 μm). The pure fractions were collected and the solvent was evaporated. The residue (0.11 g, 100%) was crystallized from diethyl ether. The precipitate was filtered off and dried. Yield 0.033 g of compound 14 (diastereoisomer B) (33%, M.P.: 189° C.).

Example B3 a) Preparation of Compound 15

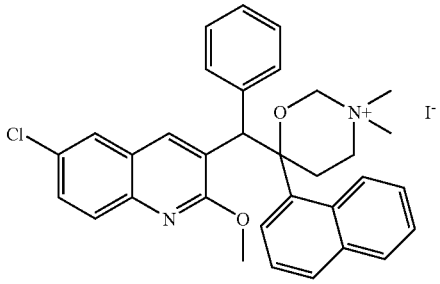

Compound 15

A mixture of compound 3 (diastereoisomer A prepared according to example B1) (0.1 mmol) and iodomethane (0.1 mmol) in acetone (2 ml) was stirred at room temperature for 2.5 hours. The precipitate was filtered, washed with acetone and dried. Yield: 0.031 g compound 15 (diastereoisomer A) (48%, M.P.: 211° C.)

Following compound was prepared according to the previous procedure:

Compound 16  0.046 g of diastereoisomer B (71%, M.P.: 195° C.).

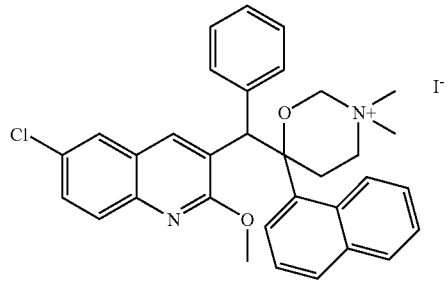

Compound 16 (diastereoisomer B)

b) Preparation of Compound 17

Compound 17

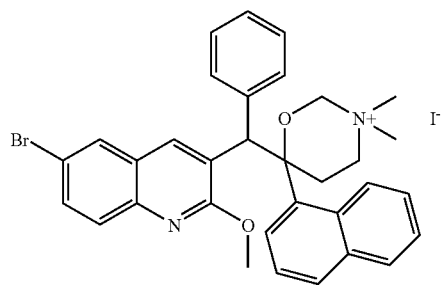

A mixture of compound 1 (0.139 mmol) and iodomethane (0.139 mmol) in acetone (3 ml) was stirred at room temperature for 3 hours. The precipitate was filtered, washed with diethylether and acetone and dried. Yield: 0.060 g of compound 17 (diastereoisomer A) (76%; M.P. 245° C.).

Following compound was prepared according to the previous procedure:

Compound 18  0.076 g of diastereoisomer B (96%, M.P.: 228° C.).

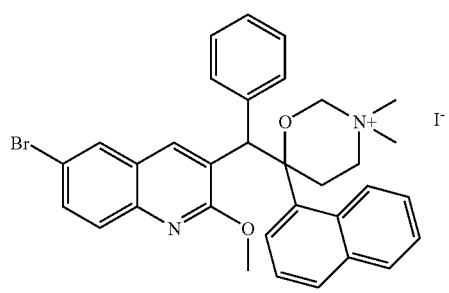

Compound 18 (diastereoisomer B)

c) Preparation of Compound 19

Compound 19

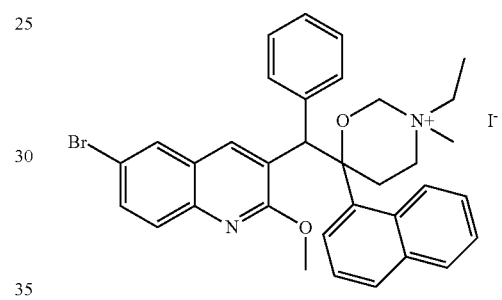

A mixture of compound 1 (0.139 mmol) and iodoethane (0.209 mmol) in acetone (3 ml) was stirred at room temperature for 24 hours. The precipitate was filtered, washed with diethylether and acetone and dried. Yield: 0.076 g of compound 19 (diastereoisomer A) (94%; M.P. 236° C.).

Following compound was prepared according to the previous procedure:

Compound 20  0.085 g of diastereoisomer B (80%, M.P.: 215° C.).

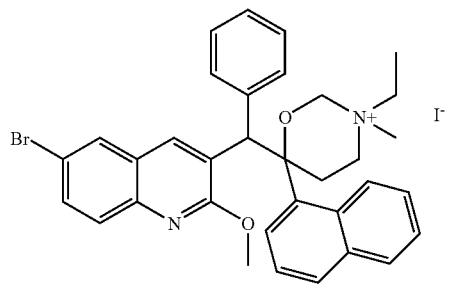

Compound 20 (diastereoisomer B)

C. Analytical Methods

The mass of the compounds was recorded with LCMS (liquid chromatography mass spectrometry). Three methods were used which are described below. The data are gathered in Table 1 below.

LCMS-Method 1

LCMS analysis was carried out (electrospray ionization in positive mode, scanning mode from 100 to 900 amu) on a Kromasil C18 column (Interchim, Montluçon, FR; 5 µm, 4.6×150 mm) with a flow rate of 1 ml/minute. Two mobile phases (mobile phase A: 30% 6.5 mM ammonium acetate+ 40% acetonitrile+30% formic acid (2 ml/l); mobile phase B: 100% acetonitrile) were employed to run a gradient condition from 100% A for 1 minute to 100% B in 4 minutes, 100% B for 5 minutes to 100% A in 3 minutes, and reequilibrate with 100% A for 2 minutes.

LCMS-Method 2

LCMS analysis was carried out (electrospray ionization in both positive and negative (pulsed) mode scanning from 100 to 1000 amu) on a Kromasil C18 column (Interchim, Montluçon, FR; 3.5 µm, 4.6×100 mm) with a flow rate of 0.8 ml/minute. Two mobile phases (mobile phase A: 35% 6.5 mM ammonium acetate+30% acetonitrile+35% formic acid (2 ml/l); mobile phase B: 100% acetonitrile) were employed to run a gradient condition from 100% A for 1 minute to 100% B in 4 minutes, 100% B at a flow rate of 1.2 ml/minute for 4 minutes to 100% A at 0.8 ml/minute in 3 minutes, and reequilibrate with 100% A for 1.5 minute.

LCMS-Method 3

LCMS analysis was carried out (electrospray ionization in both positive and negative (pulsed) mode scanning from 100 to 1000 amu) on a Sunfire C18 column (Waters, Millford USA; 3.5 µm, 4.6×100 mm) with a flow rate of 0.8 ml/minute. Two mobile phases (mobile phase A: 35% 6.5 mM ammonium acetate+30% acetonitrile+35% formic acid (2 ml/l); mobile phase B: 100% acetonitrile) were employed to run a gradient condition from 100% A for 1 minute to 100% B in 4 minutes, 100% B at a flow rate of 1.2 ml/minute for 4 minutes to 100% A at 0.8 ml/minute in 3 minutes, and reequilibrate with 100% A for 1.5 minute.

TABLE 1

| No. | LCMS parent peak LCMS-method |
|---|---|
| Intermediate 11 | 1 |
| Intermediate 12 | 1 |
| Intermediate 27 | 3 |
| Intermediate 33 | 1 |
| Intermediate 34 | 1 |
| Intermediate 37 | 3 |
| Compound 2 | 3 |
| Compound 3 | 2 |
| Compound 4 | 2 |
| Compound 5 | 3 |
| Compound 6 | 3 |
| Compound 9 | 3 |
| Compound 10 | 2 |
| Compound 11 | 3 |
| Compound 12 | 3 |
| Compound 13 | 3 |

Pharmacological Examples

Preparation of Bacterial Suspensions for Susceptibility Testing

The bacteria used in this study were grown overnight in flasks containing 100 ml Mueller-Hinton Broth (Becton Dickinson—cat. no. 275730) in sterile de-ionized water, with shaking, at 37° C. Stocks (0.5 ml/tube) were stored at 70° C. until use. Bacteria titrations were performed in microtiter plates and colony forming units (CFUs) were determined. In general, an inoculum level of approximately 100 CFUs was used for susceptibility testing.

Anti bacterial Susceptibility Testing: $IC_{90}$ Determination Microtitre Plate Assay Flat-bottom, sterile 96-well plastic microtiter plates were filled with 180 µl of sterile deionized water, supplemented with 0.25% BSA. Subsequently, stock solutions (7.8× final test concentration) of compounds were added in 45 µl volumes in column 2. Serial five-fold dilutions (45 µl in 180 µl) were made directly in the microtiter plates from column 2 to reach column 11. Untreated control samples with (column 1) and without (column 12) inoculum were included in each microtiter plate. Depending on the bacteria type, approximately 10 to 60 CFU per well of bacteria inoculum (100 TCID50), in a volume of 100 µl in 2.8× Mueller-Hinton broth medium, was added to the rows A to H, except column 12. The same volume of broth medium without inoculum was added to column 12 in row A to H. The cultures were incubated at 37° C. for 24 hours under a normal atmosphere (incubator with open air valve and continuous ventilation). At the end of incubation, one day after inoculation, the bacterial growth was quantitated fluorometrically. Therefore resazurin (0.6 mg/ml) was added in a volume of 20 µl to all wells 3 hours after inoculation, and the plates were re-incubated overnight. A change in colour from blue to pink indicated the growth of bacteria. The fluorescence was read in a computer-controlled fluorometer (Cytofluor Biosearch) at an excitation wavelength of 530 nm and an emission wavelength of 590 nm. The % growth inhibition achieved by the compounds was calculated according to standard methods. The $IC_{90}$ (expressed in µg/ml) was defined as the 90% inhibitory concentration for bacterial growth. The results are shown in Table 2.

Agar Dilution Method.

$MIC_{99}$ values (the minimal concentration for obtaining 99% inhibition of bacterial growth) can be determined by performing the standard Agar dilution method according to NCCLS standards* wherein the media used includes Mueller-Hinton agar.

*Clinical laboratory standard institute. 2005. Methods for dilution Antimicrobial susceptibility tests for bacteria that grows Aerobically: approved standard-sixth edition Time Kill Assays Bactericidal or bacteriostatic activity of the compounds may be determined in a time kill assay using the broth microdilution method*. In a time kill assay on *Staphylococcus aureus* and methicillin resistant *S. aureus* (MRSA), the starting inoculum of *S. aurues* and MRSA is $10^6$ CFU/ml in Muller Hinton broth. The antibacterial compounds are used at the concentration of 0.1 to 10 times the MIC (i.e. $IC_{90}$ as determined in microtitre plate assay). Wells receiving no antibacterial agent constitute the culture growth control. The plates containing the microorganism and the test compounds are incubated at 37° C. After 0, 4, 24, and 48 hrs of incubation samples are removed for determination of viable counts by serial dilution ($10^{-1}$ to $10_{-6}$) in sterile PBS and plating (200 µl) on Mueller Hinton agar. The plates are incubated at 37° C. for 24 hrs and the number of colonies are determined. Killing curves can be constructed by plotting the $\log_{10}$CFU per ml versus time. A bactericidal effect is commonly defined as 3-$\log_{10}$ decrease in number of CFU per ml as compared to untreated inoculum. The potential carryover effect of the drugs is removed by serial dilutions and counting the colonies at highest dilution used for plating. No carryover effect is observed at the dilution of $10^{-2}$ used for plating. This results in limit of detection $5 \times 10^2$ CFU/ml or <2.7 log CFU/ml.

*Zurenko, G. E. et al. In vitro activities of U-100592 and U-100766, novel oxazolidinone antibacterial agents. *Antimicrob. Agents Chemother.* 40, 839-845 (1996).

Determination of Cellular ATP Levels

In order to analyse the change in the total cellular ATP concentration (using ATP bioluminescence Kit, Roche), assays are carried out by growing a culture of *S. aureus* (ATCC29213) stock in 100 ml Mueller Hinton flasks and incubate in a shaker-incubator for 24 hrs at 37° C. (300 rpm). Measure $OD_{405}$ nm and calculate the CFU/ml. Dilute the cultures to $1 \times 10^6$ CFU/ml (final concentration for ATP measurement: $1 \times 10^5$ CFU/100 µl per well) and add test compound at 0.1 to 10 times the MIC (i.e. $IC_{90}$ as determined in microtitre plate assay). Incubate these tubes for 0, 30 and 60 minutes at 300 rpm and 37° C. Use 0.6 ml bacterial suspension from the snap-cap tubes and add to a new 2 ml eppendorf tubes. Add 0.6 ml cell lysis reagent (Roche kit), vortex at max speed and incubate for 5 minutes at room temperature. Cool on ice. Let the luminometer warm up to 30° C. (Luminoskan Ascent Labsystems with injector). Fill one column (=6 wells) with 100 µl of the same sample. Add 100 µl Luciferase reagent to each well by using the injector system. Measure the luminescence for 1 sec.

TABLE 2

$IC_{90}$ values (µg/ml) determined according to the Microtitre plate assay.

| Comp No. | STA 29213 | SPN 6305 | SPY 8668 | SMU 33402 | EFA 29212 | LMO 49594 | BSU 43639 | ECO 35218 | PAE 27853 | STA RMETHIC | STA 25923 | STA 43300 | EFA 14506 | ECO 1403 | ECO 25922 |
|---|---|---|---|---|---|---|---|---|---|---|---|---|---|---|---|
| 8 | 12.7 | 12.7 | 12.7 | | 12.7 | 12.7 | 12.7 | | 10.0 | 12.7 | 12.7 | | 40.0 | | |
| 10 | 12.7 | 1.1 | 10.1 | 12.7 | 12.7 | 10.1 | 2.5 | | 12.7 | 50.5 | 12.7 | | | | |
| 3 | 12.8 | 12.8 | 12.8 | | 12.8 | 12.8 | 12.8 | | 12.8 | 12.8 | 12.8 | | | | |
| 14 | 12.8 | 12.8 | 12.8 | | 12.8 | 12.8 | 12.8 | | 12.8 | 12.8 | 12.8 | | 12.8 | | |
| 6 | 13.6 | 2.7 | 13.6 | | 13.6 | | 13.6 | | 13.6 | 54.1 | 13.6 | | | | |
| 12 | 13.6 | 12.1 | 10.8 | 10.8 | 13.6 | 13.6 | | | 13.6 | 13.6 | 13.6 | | | | |
| 7 | 13.9 | 13.9 | 13.9 | | 13.9 | | | | 13.9 | | | | | | |
| 13 | 14.8 | 13.2 | 14.8 | | 14.8 | | | | 14.8 | | | | | | |
| 5 | 48.9 | 10.9 | 8.7 | 24.5 | 48.9 | 48.9 | 48.9 | | 48.9 | 48.9 | 48.9 | | | | |
| 11 | 48.9 | 4.9 | 19.5 | 48.9 | 48.9 | 48.9 | 48.9 | | 48.9 | 48.9 | 48.9 | | | | |
| 4 | 50.5 | 1.0 | 20.1 | 20.1 | 50.5 | 25.3 | 50.5 | | 50.5 | 50.5 | 50.5 | | | | |
| 9 | 55.1 | 4.9 | 55.1 | | 55.1 | 55.1 | 55.1 | | 55.1 | 55.1 | 55.1 | | | | |
| 2 | 55.1 | 5.5 | 55.1 | | 55.1 | 55.1 | 55.1 | | 55.1 | 55.1 | 55.1 | | | | |
| 1 | 55.4 | 5.5 | 44.0 | 44.0 | 55.4 | 44.0 | 44.0 | | 44.0 | 55.4 | 55.4 | | | | |
| 18 | 2.3 | 1.8 | 1.8 | | 1.8 | | | | 2.0 | 2.3 | | | | | |
| 17 | 1.8 | 1.8 | 1.8 | | 1.8 | | | | 2.0 | 2.3 | | | | | |
| 19 | 0.4 | 0.5 | 1.8 | | 1.8 | | | | 3.7 | 2.3 | | | | | |
| 20 | 0.5 | 1.8 | 2.1 | | 1.8 | | | | 4.6 | 2.3 | | | | | |
| 16 | 1.9 | 5.2 | 1.9 | 2.1 | 2.6 | 1.7 | 10.5 | 41.6 | 10.5 | 2.1 | 1.9 | 41.6 | 2.1 | 13.2 | |
| 15 | 1.86 | 2.3 | 1.9 | 1.9 | 2.1 | 2.1 | 2.1 | 41.6 | 9.3 | 1.9 | 2.1 | 9.3 | 2.1 | 10.5 | 10.5 |
| 21 | 14.8 | 14.8 | 14.8 | | 14.8 | | | | 14.8 | | | | | | |

BSU 43639 means *Bacillus subtilis* (ATCC43639);
ECO 25922 means *Escherichia coli* (ATCC25922);
ECO 35218 means *Escherichia coli* (ATCC35218);
ECO 1403 means *Escherichia coli* (ATCC1403);
EFA 14506 means *Enterococcus faecalis* (ATCC14506);
EFA 29212 means *Enterococcus faecalis* (ATCC29212);
LMO 49594 means *Listeria monocytogenes* (ATCC49594);
PAE 27853 means *Pseudomonas aeruginosa* (ATCC27853);
SMU 33402 means *Streptococcus mutans* (ATCC33402);
SPN 6305 means *Streptococcus pneumoniae* (ATCC6305);
SPY 8668 means *Streptococcus pyogenes* (ATCC8668);
STA 43300 means *Staphylococcus aureus* (ATCC43300);
STA 25923 means *Staphylococcus aureus* (ATCC25923);
STA 29213 means *Staphylococcus aureus* (ATCC29213);
STA RMETH means methicilline resistant *Staphylococcus aureus* (MRSA) (a clinical isolate from the University of Antwerp).
ATCC means American type tissue culture.

The invention claimed is:
1. A method for treatment of a bacterial infection in a mammal, said method comprising administering to said mammal an effective amount of a compound of Formula (Ia) and (Ib)

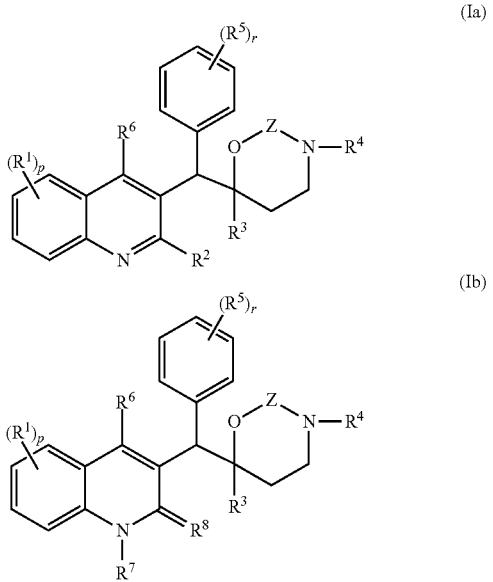

a pharmaceutically acceptable acid or base addition salt thereof or a quaternary amine thereof, a stereochemically isomeric form thereof, wherein $R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl;

p is an integer equal to 1, 2, 3 or 4;

$R^2$ is hydrogen, hydroxy, mercapto, alkyloxy, alkyloxyalkyloxy, alkylthio, mono or di(alkyl)amino or a radical of formula

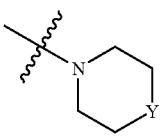

wherein Y is $CH_2$, O, S, NH or N-alkyl;

$R^3$ is alkyl, Ar, Ar-alkyl, Het or Het-alkyl;

$R^4$ is hydrogen, alkyl or benzyl;

$R^5$ is hydrogen, halo, haloalkyl, hydroxy, Ar, alkyl, alkyloxy, alkylthio, alkyloxyalkyl, alkylthioalkyl, Ar-alkyl or di(Ar)alkyl; or two vicinal $R^5$ radicals may be taken together to form together with the phenyl ring to which they are attached a naphthyl;

r is an integer equal to 1, 2, 3, 4 or 5; and $R^6$ is hydrogen, alkyl, Ar or Het;

$R^7$ is hydrogen or alkyl;

$R^8$ is oxo; or $R^7$ and $R^8$ together form the radical —CH=CH—N=;

Z is $CH_2$ or C(=O);

alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with hydroxy, alkyloxy or oxo;

Ar is a homocycle selected from the group of phenyl, naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, aminocarbonyl, morpholinyl and mono- or dialkylaminocarbonyl;

Het is a monocyclic heterocycle selected from the group of N-phenoxypiperidinyl, piperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from the group of quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydro-benzo[1,4]dioxinyl or benzo[1,3]dioxolyl; each monocyclic and bicyclic heterocycle may optionally be substituted on a carbon atom with 1, 2 or 3 substituents, each substituent independently selected from the group of halo, hydroxy, alkyl or alkyloxy;

halo is a substituent selected from the group of fluoro, chloro, bromo and iodo and haloalkyl is a straight or branched saturated hydrocarbon radical having from 1 to 6 carbon atoms or a cyclic saturated hydrocarbon radical having from 3 to 6 carbon atoms or a cyclic saturated hydrocarbon radical having from 3 to 6 carbon atoms attached to a straight or branched saturated hydrocarbon radical having from 1 to 6 carbon atoms; wherein one or more carbon atoms are substituted with one or more halo atoms;

provided that the bacterial infection is other than a Mycobacterial infection.

2. The method according to claim 1 wherein $R^1$ is hydrogen, halo, Ar, Het, alkyl or alkyloxy.

3. The method according to claim 2 wherein $R^1$ is halo.

4. The method according to claim 1 wherein p is equal to 1.

5. The method according to claim 1 wherein $R^2$ is alkyloxy.

6. The method according to claim 1 wherein $R^3$ is naphthyl or phenyl, each optionally substituted with 1 or 2 substituents.

7. The method according to claim 1 wherein $R^4$ is alkyl.

8. The method according to claim 1 wherein $R^5$ is hydrogen or halo.

9. The method according to claim 1 wherein r is 1.

10. The method according to claim 1 wherein $R^6$ is hydrogen.

11. The method according to claim 1 wherein Z is $CH_2$.

12. The method according to claim 1 wherein the compound is a compound of Formula (Ia).

13. The method according to claim 1 wherein $R^1$ is hydrogen; halo; alkyl; Ar or Het; $R^2$ is alkyloxy; $R^3$ is naphthyl or phenyl, each optionally substituted with 1 or 2 halo; $R^4$ is alkyl; $R^5$ is hydrogen or halo; $R^6$ is hydrogen; Z is $CH_2$.

14. The method according to claim 1 wherein the bacterial infection is an infection with a gram-positive bacterium.

15. The method according to claim 1 wherein alkyl is $C_{1-6}$alkyl.

16. The method according to claim 1 wherein the bacterial infection is an infection with Staphylococci, Enterococci or Streptococci.

17. The method according to claim 1 wherein the bacterial infection is an infection with methicillin resistant *Staphylo-*

*coccus aureus* (MRSA), methicillin resistant coagulase negative staphylococci (MRCNS), penicillin resistant *Streptococcus pneumoniae* or multiple resistant *Enterococcus faecium*.

18. The method according to claim 1 wherein the bacterial infection is an infection with *Staphylococcus aureus* or *Streptococcus pneumoniae*.

19. The method according to claim 1 wherein the bacterial infection is an infection with methicillin resistant *Staphylococcus aureus* (MRSA).

* * * * *